US008682000B2

(12) United States Patent
Vau

(10) Patent No.: US 8,682,000 B2
(45) Date of Patent: Mar. 25, 2014

(54) METHOD AND DEVICE FOR NARROW-BAND NOISE SUPPRESSION IN A VEHICLE PASSENGER COMPARTMENT

(75) Inventor: Bernard Vau, Saint Maur des Fosses (FR)

(73) Assignee: Ixblue, Marly le Roi (FR)

( * ) Notice: Subject to any disclaimer, the term of this patent is extended or adjusted under 35 U.S.C. 154(b) by 329 days.

(21) Appl. No.: 13/322,777

(22) PCT Filed: Aug. 31, 2009

(86) PCT No.: PCT/FR2009/051647

§ 371 (c)(1), (2), (4) Date: Nov. 28, 2011

(87) PCT Pub. No.: WO2010/136661

PCT Pub. Date: Dec. 2, 2010

(65) Prior Publication Data

US 2012/0070013 A1 Mar. 22, 2012

(30) Foreign Application Priority Data

May 28, 2009 (FR) ...................................... 09 02585

(51) Int. Cl.
*A61F 11/06* (2006.01)
*G10K 11/16* (2006.01)
*H03B 29/00* (2006.01)

(52) U.S. Cl.
USPC ... 381/71.4; 381/71.1; 381/71.11; 381/71.14; 381/86; 381/94.1

(58) Field of Classification Search
USPC .................. 381/71.1, 71.2, 71.3, 71.4, 71.11, 381/71.14, 86, 94.1, 94.3; 181/206, 296
See application file for complete search history.

(56) References Cited

U.S. PATENT DOCUMENTS 5,337,366 A * 8/1994 Eguchi et al. .............. 381/71.11
5,831,401 A 11/1998 Coleman et al.
2004/0223543 A1 11/2004 Tsai

FOREIGN PATENT DOCUMENTS

EP 0 578 212 A2 1/1994

OTHER PUBLICATIONS

Amara, Kabamba, Ulsoy: "Adaptive sinusoidal disturbance rejection in linear discrete-time systems—Part II: Experiments" Journal of Dynamic Systems, Measurement, and Control, vol. 121, No. 4, Dec. 1, 1999, pp. 655-659, XP008119671 the whole document.

Amara, Kabamba, Ulsoy: "Adaptive sinusoidal disturbance rejection in linear discrete-time systems—part 1: Theory" Journal of Dynamic Systems Measurement and Control, vol. 121, No. 4, Dec. 1, 1999, pp. 648-654, XP008119190 the whole document.

Landau, I. D., Constantinescu, A.,Rey, D.: "Adaptive narrow band disturbance rejection applied to an active suspension—an internal model principle approach" Automatica, Jan. 24, 2005, pp. 563-574, XP002570052.

McEver, M. A. et al.: "Adaptive control for interior noise control in rockets fairings" AIAA, Nov. 18, 2003, pp. 3782-3791, XP008119175.

International Search Report, dated Sep. 4, 2010, from corresponding PCT application.

* cited by examiner

*Primary Examiner* — Vivian Chin
*Assistant Examiner* — Paul Kim
(74) *Attorney, Agent, or Firm* — Young & Thompson

(57) ABSTRACT

A method and a device for suppressing noise in the passenger compartment of a vehicle, which include at least one transducer, a programmable computer, at least one acoustic sensor, the computer being configured such as to apply an electro-acoustic model of the passenger compartment to a correcting system model including a central controller with fixed coefficients joined to a block of variable coefficients, including a Youla parameter in the form of a Youla block Q. The first phase includes determining and calculating the electro-acoustic model and the control law for at least one predetermined noise frequency. In a second phase, in real time, the computer applies the control law to the electro-acoustic model in accordance with the current frequency of the noise to be suppressed.

18 Claims, 8 Drawing Sheets

METHOD AND DEVICE FOR NARROW-BAND NOISE SUPPRESSION IN A VEHICLE PASSENGER COMPARTMENT

The present invention relates to a method and a device for noise rejection in a passenger compartment of a vehicle, in particular a car, through active control. It finds applications in the industrial field of the motor vehicles, this term being understood in its broadest sense, including in particular light vehicles, heavy vehicles, road vehicles, rail vehicles, boats, canal-boats, submarines, and in the field of the electroacoustic devices, such as for example car radios to which such a function may be added.

Some acoustic noises occurring in a passenger compartment of a vehicle may have a wide spectrum, and other may on the contrary be approximately mono-frequency. This in particular the case of the noise generated by the rotation of the crankshaft, known as the "booming noise" that is expressed by a noise whose spectrum is composed of lines whose frequencies are proportional to the frequency of rotation of the crankshaft, with one fundamental and harmonics.

These frequencies vary according to the crankshaft's rotational speed, but they can nevertheless be accurately known by the information coming from the tachometer generally integrated in the vehicle.

It has already been proposed to reduce, or even to suppress, those noises through active acoustic means. It can be mentioned on that subject a statement of the art in the field of active control applied to automotive vehicles, provided by Elliot in December 2008, in an article whose title is "A review of active noise and vibration control in road vehicle" (ISVR technical memorandum n° 981—University of Southampton).

Two main structures of acoustic active control exist. Firstly, a so-called "feedforward" or pre-compensation structure. Such structure needs a loud-speaker, an error microphone at which it is desired to cancel the noise, and a controller receiving a reference signal, correlated with the signal to be cancelled, producing a correction signal sent to the loud-speaker. Such structure is schematically shown in FIG. 1 illustrating the prior art. Such structure has notably given rise to a series of algorithms based on the "Least Mean Square" (LMS) method: Fx-LMS, FR-LMS, the purpose of which is to minimize, in the sense of the least squares, the signal coming from the error microphone, and this by processing the reference signal.

Still in the case of a so-called "feedforward" structure, reference can be made to the article of Sano et al., "NV countermeasure technology for a cylinder—On-Demand Engine-Development of active booming noise control applying adaptive notch filter" (SAE 2004). The authors present an algorithm based on a band-stop ("notch") adaptive filter, with the noise attenuation frequency being known. The device is based on an algorithm whose structure is of the "feedforward" type, called FR-SAN, which is an adaptation of the FR-LMS algorithm, in case the noise to be attenuated is of the mono-frequency type. When this algorithm is implemented, the problems arising when the transfer function of the passenger compartment varies, for example as a function of the number of passengers, are not taken into account. Moreover, with such algorithm, it is not possible to know in another way than experimentally the response of the control system at other frequencies than the frequency at which it operates.

Secondly, a so-called "feedback" or counter-reaction structure. Such structure is schematically shown in FIG. 2 illustrating the prior art. Such structure, unlike the so-called "feed-forward" structure, does not need a reference signal. It is then a conventional feedback structure, and all the tools of the conventional automatic control engineering (in particular, robustness measurement, stability analysis, performance) can be used. In particular, an analysis of the closed loop system robustness with respect to the variation of the passenger-compartment transfer function may be performed. The frequency response of the system may also be studied, not only at the disturbance rejection frequency, but also at other frequencies.

The present invention belongs to this second type of so-called "feedback" structure. More particularly, it relates to a real-time active method for attenuating, through feedback, a narrow-band noise, essentially mono-frequency at least one determined frequency, in a vehicle passenger compartment, by emitting a sound through at least one transducer, typically a loud-speaker, controlled by a signal u(t) or U(t) according to a SISO or MIMO case respectively generated by a programmable calculator, as a function of a signal of acoustic measurements y(t) or Y(t) according to the case, performed by at least one acoustic sensor, typically a microphone, wherein the use of one sensor corresponds to SISO, single input single output, a mono-variable, case and the use of several sensors corresponds to MIMO, a multi-inputs-multi-outputs-variables case, and, in a first phase of design, the electroacoustic response of the unit formed by the passenger compartment, the transducer and the sensor, is modeled by an electroacoustic model as an electroacoustic transfer function that is determined and calculated, a control law being then determined and calculated from an global model of the system in which the control law is applied to the electroacoustic transfer function whose output additionally receives a noise signal to be attenuated p(t) to give the signal y(t) or Y(t) in said design phase, said control law making it possible to produce the signal u(t) or U(t) as a function of the acoustic measurements y(t) or Y(t), and in a second phase of use, said calculated control law is used in the calculator to produce the signal u(t) or U(t) then sent to the transducer as a function of the signal y(t) or Y(t) received from the sensor for attenuating said noise.

According to the invention, a control law is implemented, which comprises the application of a Youla parameter to a central controller and which is such that only the Youla parameter has coefficients that depend on the frequency of the noise to be attenuated in said control law, the central controller having fixed coefficients, the Youla parameter being in the form of an infinite impulse response filter, and, after determination and calculation of the control law, at least said variable coefficients are stored into a memory of the calculator, preferably in a table as a function the determined noise frequency(ies) p(t) used in the design phase and in the use phase, in real time:

- the current frequency of the noise to be attenuated is collected,
- the calculator is caused to calculate the control law, comprising the central controller with the Youla parameter, using as the Youla parameter the memorized coefficients of a determined frequency corresponding to the current frequency of the noise to be attenuated.

In other words, a control law is implemented, which comprises a part with fixed coefficients, called the central controller, and a part with coefficients varying as a function of the frequency of the noise to be attenuated, which is here a Youla parameter, the part of the controller with the variable coefficients being an infinite impulse response filter and, after determination and calculation of the control law, at least said variable coefficients are stored into a memory of the calculator, preferably in a table as a function the determined noise frequency(ies) p(t) used in the design phase and in the use phase, in real time: the current frequency of the noise to be attenuated is collected, and the calculator is caused to calculate the control law, comprising the fixed-coefficient central controller with the variable-coefficient part, using as the variable-coefficient part the memorized coefficients of a determined frequency corresponding to the current frequency of the noise to be attenuated. Therefore, within the framework of the invention, for the attenuation of the noise at least one determined frequency, a fixed-coefficient central controller is implemented, to which is adjoined a variable-coefficient block that is a Youla parameter in the form of a Youla block Q.

Within the framework of the invention, the term "signal" relates both to analogic signals, as for example the electrical signal outputted from the microphone itself, and to digital signals, as for example the output signal of the Youla block $Q(q^{-1})$. Moreover, it will be understood that the terms "transducer" and "sensor" are used in a generic and functional meaning and that, in practice, interface electronic circuits, such as notably analogic-digital or digital-analogic converters, spectrum antialiasing filter(s), amplifier(s) (for the loudspeaker(s) and microphone(s)), are associated therewith. The term "signal" also covers the SISO, single input single output, mono-variable (one sensor and thus a single one input of acoustic measurements) and MIMO, multi-inputs-multi-outputs-variables (several sensors and thus several inputs of acoustic measurements) cases, whatever the number of loudspeaker(s). Thus, the invention may apply both to a SISO, single input single output, mono-variable case (a single one microphone, i.e. a single one place at which the noise will be attenuated in the passenger compartment), and to MIMO, multi-inputs-multi-outputs-variables cases (several microphones, i.e. as many places at which the noise will be attenuated). It is also understood that the invention applies to the attenuation of both a noise that is at a particular frequency substantially fixed over time (for example, the noise of a truck refrigeration compressor), and a noise whose frequency may evolve over time, and in this case, in the design phase, it is preferable to determine and calculate Youla parameters, block $Q(q^{-1})$, for several determined frequencies, so as to take, during the use phase, the result of calculation of the Youla parameter for a determined frequency that corresponds (is equal or near, which, in fact, corresponds the best or is otherwise interpolated) to the current frequency of the noise to be attenuated. It is understood that the finer the frequency mesh will be, the highest the chance will be to find a result of calculation of the Youla parameter with a determined frequency that corresponds to the frequency of the current noise to be attenuated. Indeed, it will be seen that in the control law, only the Youla parameter is variable (in practice, the coefficients thereof) as a function of the frequency of the noise, unlike the coefficients of the central controller that remain fixed and independent of the noise frequency.

It can be noted that the Youla parameterization has already been used for the purpose of sinusoidal disturbance rejection, in a completely different field: the control of vibrations of an active suspension. The corresponding article is: "Adaptive narrow disturbance applied to an active suspension—an internal model approach" (Automatica 2005), whose authors are I.D. Landau et al. In this latest device, the Youla parameter is in the form of a finite impulse response filter (transfer function with a single one polynomial, without denominator), whereas in the present invention, it will be seen that this Youla parameter is in the form of an infinite impulse response filter (transfer function with a numerator and a denominator). Moreover, in this article, the calculation of the coefficients of the Youla parameter is done by means of an adaptive device, i.e. the information about the disturbance frequency is not known, unlike in the present invention where this frequency is known based on measurements, in particular a revolution counter, and where the coefficients of the Youla parameters are stored in tables to be used in real time. The device and the method according to the invention provide the control law with a far greater robustness. In the particular case of the invention, it corresponds to an insensitivity of the control law to the parameter variations of the electroacoustic model, i.e. to the variations of the configuration of the passenger compartment, which, from the industrial point of view, is a fundamental element.

It may also be mentioned the article "Adaptive control for interior noise control in rocket fairings", Mark A. Mcever, $44^{th}$ AIAA/ASME/ASCE/AHS Structures, structural dynamics and material conference, 7-10 Apr. 2003. Herein again, the Youla parameter is a finite impulse response (FIR) filter, which causes problems regarding the system robustness, the algorithm is adaptive and is not dedicated to the rejection of a frequency in particular.

Finally, in the field of the control of vibrations in an automotive vehicle, it may also be mentioned the article: "Active control of engine-induced vibrations in automotive vehicles using disturbance observer gain scheduling", in control engineering practice 12 (2004) 1029-1039, Bohn et al. The control law presented uses a state observer, several elements of which vary as a function of the frequency to be rejected, which leads to the fact that the control law has a far greater number of varying parameters than the optimal number. On the other hand, the present invention guarantees that the number of varying parameters of the control law is a minimum.

In various embodiments of the invention, the following means are used, either alone or in any technically possible combination:

the design phase is implemented in a programmable calculator, the Youla parameter is determined and calculated by discretization of a continuous transfer function of the second order, in the second time of the design phase, the polynomials $Ro(q^{-1})$ and $So(q^{-1})$ of the central controller are determined and calculated so that said central controller alone guarantees gain and phase margins, with no purpose of disturbance rejection, In the SISO, single input single output, mono-variable case, in the design phase:

a)—in a first time, a linear electroacoustic model is used, the electroacoustic model being in the form of a discrete rational electroacoustic transfer function, and said electroacoustic model is determined and calculated by acoustic excitation of the passenger compartment by the transducer and acoustic measurements by the sensor, then application of a linear system identification process with the measures and the model, b)—in a second time, a central controller is implemented, which is applied to the determined and calculated electroacoustic model, the central controller being in the form of a RS controller of two blocks $$\frac{1}{So(q^{-1})}$$

and $Ro(q^{-1})$, in the central controller, the block $$\frac{1}{So(q^{-1})}$$

producing the signal u(t) and receiving as an input the inverted output signal of the block $Ro(q^{-1})$, said block $Ro(q^{-1})$ receiving as an input the signal y(t) corresponding to the sum of the noise p(t) and of the output of the electroacoustic transfer function of the electroacoustic model, and the central controller is determined and calculated, c)—in a third time, a Youla parameter, which is thus a variable-coefficient transfer block, is adjoined to the central controller to form the control law, the Youla parameter being in the form of a block $Q(q^{-1})$, a infinite impulse response filter, with $$Q(q^{-1}) = \frac{\beta(q^{-1})}{\alpha(q^{-1})}$$

adjoined to the central RS controller, said Youla block $Q(q^{-1})$ receiving a noise estimation obtained by calculation from the signals u(t) and y (t) and as a function of the electroacoustic transfer function and the output signal of said Youla block $Q(q^{-1})$ being subtracted from the inverted signal of $Ro(q^{-1})$ sent to the input of the block $$\frac{1}{So(q^{-1})}$$

of the central RS controller, and the Youla parameter, thus the variable-coefficient transfer block, in the control law comprising the central controller with which is associated the Youla parameter, is determined and calculated for at least one noise frequency p(t), including at least the determined frequency of the noise to be attenuated, and in the use phase, in real time:

the current frequency of the noise to be attenuated is collected, the calculator is caused to calculate the control law, comprising the RS controller with the Youla parameter, using as the Youla parameter the coefficients that have been calculated for a noise frequency corresponding to the current frequency of the noise to be attenuated, the coefficients of $Ro(q^{-1})$ and $So(q^{-1})$ being fixed coefficients, in the design phase, SISO, single input single output, mono-variable case, the following operations are performed:

a)—in a first time, the passenger compartment is acoustically excited by applying to the transducer an excitation signal whose spectral density is substantially uniform over an effective band of frequencies, b)—in a second time, the polynomials $Ro(q^{-1})$ and $So(q^{-1})$ of the central controller are determined and calculated, so that said central controller is equivalent to a controller calculated by poles placement of the closed loop in the application of the central controller to the electroacoustic transfer function, n poles of the closed loop being placed onto the n poles of the transfer function of the electroacoustic system, c)—in a third time, the numerator and denominator of the Youla block $Q(q^{-1})$ in the control law are determined and calculated for at least one noise frequency p(t), including at least the determined frequency of the noise to be attenuated, as a function of a criterion of attenuation, the block $Q(q^{-1}$ being expressed in the form of a ratio $$\frac{\beta(q^{-1})}{\alpha(q^{-1})},$$

so as to obtain coefficient values of the polynomials $\alpha(q^{-1})$ and $\beta(q^{-1})$ for the/each frequency, the calculation of $\beta(q^{-1})$ and $\alpha(q^{-1})$ being performed by obtaining a discrete transfer function $$\frac{HS(q^{-1})}{\alpha(q^{-1})}$$

resulting from the discretization of a continuous transfer function of the second order, the polynomial $\beta(q^{-1})$ being calculated by solving a Bezout equation, and in the use phase, in real time, the following operations are performed:

the calculator is caused to calculate the control law, fixed-coefficient central controller with variable-coefficient Youla parameter, to produce the signal u(t) sent to the transducer, as a function of the acoustic measurements y(t) and using for the Youla block $Q(q^{-1})$ the coefficient values of the polynomials $\alpha(q^{-1})$ and $\beta(q^{-1})$ determined and calculated for a determined frequency corresponding to the current frequency, the calculation of the noise estimation is obtained by applying the numerator of the electroacoustic transfer function to u(t) and subtracting the result to the application of y(t) to the denominator of the electroacoustic transfer function, for the electroacoustic model is used an electroacoustic transfer function of the form:

$$\frac{y(t)}{u(t)} = \frac{q^{-d}B(q^{-1})}{A(q^{-1})}$$

where d is the number of delay sampling periods of the system, B and A are polynomials in $q^{-1}$ of the form:

$$B(q^{-1})=b_0+b_1\cdot q^{-1}+\ldots b_{nb}\cdot q^{-nb}$$

$$A(q^{-1})=1+a_1\cdot q^{-1}+\ldots a_{na}\cdot q^{-na}$$

where $b_i$ and $a_i$ are scalar quantities, and $q^{-1}$ is the delay operator of a sampling period, and the calculation of the noise estimation is obtained by applying the function $q^{-d}B(q^{-1})$ to u(t) and subtracting the result from the application of y(t) to the function $A(q^{-1})$, for the time b), the polynomials $Ro(q^{-1})$ and $So(q^{-1})$ of the central controller are determined and calculated by a pole placement method, n dominant poles of the closed loop provided with the central controller being chosen equal to the n poles of the electroacoustic transfer function and m auxiliary poles being poles located in high frequency, in the design phase:

a)—in a first time, a linear electroacoustic model is used, wherein the electroacoustic model is in the form of a state representation of matrix blocks H, W, G and $q^{-1}\cdot I$, G being a transition matrix, H being an input matrix, W being an output matrix, and I being the identity matrix, wherein said state representation can be expressed by a recurrence equation:

$$X(t+Te)=G\cdot X(t)+H\cdot U(t)$$

$$Y(t)=W\cdot X(t)$$

with X(t): state vector, U(t): inputs vector; Y(t): outputs vector, and said electroacoustic model is determined and calculated by acoustic excitation of the passenger compartment by the transducers and acoustic measurements by the sensors, then application of a linear system identification process with the measures and the model, b)—in a second time, a central controller applied to the determined and calculated model is implemented, the central controller being in the form of a state observer and feedback of estimated state, that iteratively expresses $\hat{X}$, a state vector of the observer, as a function of Kf, a gain of the observer, Kc a vector of feedback on the estimated state, as well as the previously determined and calculated electroacoustic model, i.e.:

$$\hat{X}(t+Te)=G\cdot\hat{X}(t)+H\cdot U(t)+Kf\cdot(Y(t)-W\cdot\hat{X}(t))$$

with a control $U(t)=-Kc\cdot\hat{X}(t)$ and said central controller is determined and calculated, c)—in a third time, a Youla parameter, which is thus a variable-coefficient transfer block, is adjoined to the central controller to form the control law, the Youla parameter being in the form of a MIMO, multi-inputs-multi-outputs-variables block Q, of state matrices AQ, BQ, CQ, adjoined to the central controller also expressed in the form of a state representation, block Q whose output added to the output of the central controller produces a signal that forms the opposite of U(t), and whose input receives the signal Y(t) from which is subtracted the signal $W\cdot\hat{X}(t)$, and the Youla parameter, thus the variable-coefficient transfer block, in the control law comprising the central controller with which is associated the Youla parameter, is determined and calculated for at least one noise frequency p(t), including at least the determined frequency of the noise to be attenuated, the calculation of the coefficients of the matrices AQ, BQ, CQ being performed by obtaining discrete transfer functions $$\frac{Hsi(q^{-1})}{\alpha i(q^{-1})}$$

resulting from the discretization of continuous transfer functions of the second order and by placing poles, as well as solving equations of asymptotic rejection, and, in the use phase, in real time:

the current frequency of the noise to be attenuated is collected, the calculator is caused to calculate the control law, comprising the fixed-coefficient central controller with the variable-coefficient Youla parameter, using as the Youla parameter the coefficients that have been calculated for a noise frequency corresponding to the current frequency of the noise to be attenuated, in the design phase (multi-variable case), the following operations are performed:

a)—in a first time, the passenger compartment is acoustically excited by applying to the transducers excitation signals whose spectral density is substantially uniform over an effective band of frequencies, the excitation signals being de-correlated from each other, b)—in a second time, the central controller is determined and calculated so that it is equivalent to a controller with a state observer and a feedback on the calculated state by poles placement in the application of the central controller to the electroacoustic transfer function, wherein, for that purpose, a null observer gain is chosen, i.e. Kf=0 (the observer gain is chosen equal to the null matrix), and a gain of state feedback Kc is chosen so as to introduce high-frequency poles in the loop in order to ensure the robustness of the control law provided with the Youla parameter, the calculation of Kc being for example performed by linear-quadratic (LQ) optimization, c)—in a third time, considering a representation of increased state observer, the poles of the Youla block Q in the control law are determined and calculated for at least one noise frequency P(t) including at least the determined frequency of the noise to be attenuated, as a function of criterion of attenuation, so as to obtain coefficient values of the Youla parameter for the/each frequency, and in the use phase, in real time, the following operations are performed:

the calculator is caused to calculate the control law, fixed-coefficient central controller with variable-coefficient Youla parameter, to produce the signal U(t) sent to the transducers, as a function of the acoustic measurements Y(t) and using for the Youla parameter the coefficient values determined and calculated for a determined frequency corresponding to the current frequency, in the second time, the calculation of Kc is performed by linear-quadratic (LQ) optimization, the method is adapted to a set of determined frequencies of noise to be attenuated, and the time c) is repeated for each of the determined frequencies, and, in the use phase, when no one of the determined frequencies corresponds to the current frequency of the noise to be attenuated, an interpolation is made at said current frequency for the coefficient values of the Youla block Q, based on the coefficient values of said Youla block Q that are known for the determined frequencies, the signals are sampled at a frequency Fe and, at the time a), the effective band of frequencies used for the excitation signal is substantially equal to [0, Fe/2], the excitation signal has a uniform spectral density, before the application phase, a fourth time d) is added to the design phase, for verifying the stability and the robustness of the electroacoustic system model and of the control law, central controller with Youla parameter, previously obtained at the times a) to c), by making a simulation of the control law obtained at times b) and c), applied to the electroacoustic model obtained at the time a), for the determined frequency(ies), and when a predetermined criterion of stability and/or robustness is not respected, at least the time c) is reiterated by modifying the criterion of attenuation, in the fourth time d) of the design phase, when a predetermined criterion of stability and/or robustness is not respected, the time b) is further reiterated by modifying the auxiliary poles of the closed loop, the design phase is a preliminary phase and it is performed once, preliminary to the use phase, with memorization of the determination and calculation results for use in the use phase (for example, in the SISO, single input single output, monovariable case, memorization of the coefficients of the blocks R, S and Q for the calculated control law, as well as the calculated electroacoustic transfer function, for the block Q of the coefficient tables that can be implemented because of calculations for several determined frequencies), the criterion of attenuation is selected as a function of at least one of the two following elements: the attenuation depth (amplitude) and the attenuation bandwidth, the current frequency of the noise to be attenuated is collected from a measurement of a motor revolution counter of the vehicle.

More generally, the invention also relates to a device specially adapted for the implementation of the method of the invention to attenuate a narrow-band noise, essentially mono-frequency at least one determined frequency, wherein the device comprises at least one transducer, typically a loud-speaker, controlled with a signal generated by a programmable calculator, as a function of a signal of acoustic measurements performed by at least one acoustic sensor, typically a microphone, wherein a control law has been determined and calculated in a first phase of design, said calculated control law being used, in a second phase of use, in the calculator, to produce a signal sent to the transducer, as a function of the signal received from the sensor for attenuation of said noise, and wherein the device comprises means for implementing, in the calculator, a control law comprising the application of Youla parameter to a central controller, wherein only the Youla parameter have coefficients that depend on the frequency of the noise to be attenuated in said control law, the central controller having fixed coefficients, and a memory of the calculator stores at least said variable coefficients, preferably in a table as a function of the determined noise frequency(ies) p(t) used in the design phase.

The invention also relates to a support of instructions for directly or indirectly controlling the calculator so that it operates according to the method of the invention, and in particular in real time in the use phase.

The present invention will now be further described, without thereby being limited, by the following description, with reference to the attached drawings, in which:

FIG. 1 according to the prior art is a schematic representation of a so-called "feedforward" or pre-compensation structure of a noise attenuation system;

FIG. 2 according to the prior art is a schematic representation of a so-called "feedback" or counter-reaction structure of a noise attenuation system;

FIG. 3 according to the prior art is a schematic representation of the principle diagram of an electroacoustic loop system, with a control law, for a car passenger compartment;

The principles underlying the operation of the device of active control of the noise in the passenger compartment according to the invention will now be described in further detail, wherein the device, under the control of a programmable calculator, consists of a microphone and one or several loud-speakers connected to each other and integrated in the vehicle. The loud-speakers are controlled by a control law that elaborate control signals based on the signal received from the microphone. The control law as well as the methodology for adjusting this control law will thus be described in detail. In order to simplify the explanations, in a first part, reference will be made to the simpler SISO, single input single output, mono-variable case (a single one microphone), and in a second part, to the multi-inputs-multi-outputs-variables case (several microphones).

Figure 1:
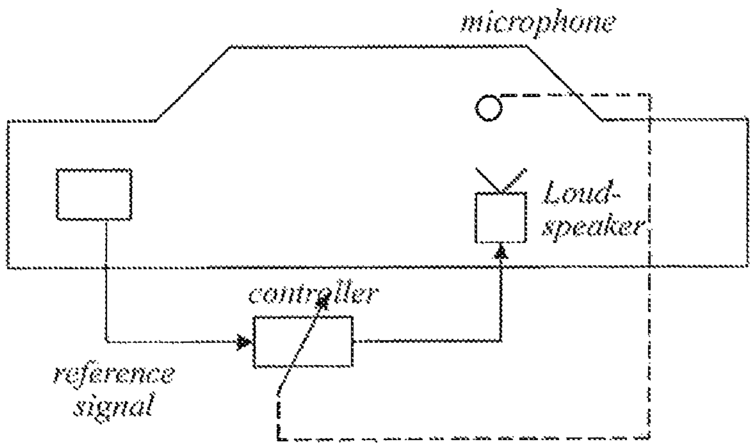
Fig. 1 PRIOR ART
Figure 2:
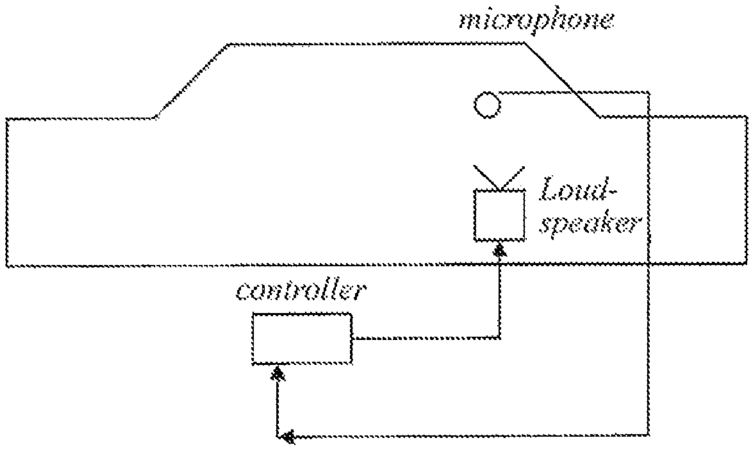
Fig. 2 PRIOR ART
Figure 3:
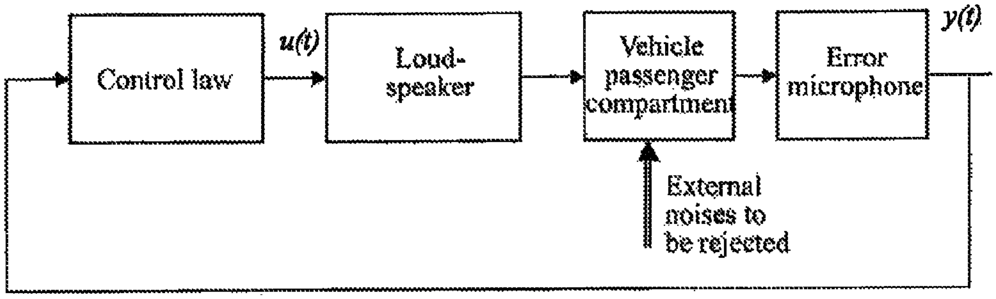

The principle diagram with control law and establishment of an electroacoustic loop in the vehicle is generally shown in FIG. 3.

To begin with, the device of the invention (and the method that is implemented therein) comprises means for rejecting a mono-frequency disturbance (noise), whose frequency is supposed to be known, tanks to external information, as for example the vehicle motor rotational speed given by a tachometer . . . .

In order to synthesize a control law, a model of the real system, consisted of the electroacoustic and acoustic elements of the passenger compartment, including the loud-speaker(s) (transducers), microphone(s) (sensor), associated electronic element(s) (amplifiers, converters . . . ), is needed. Such model, referred to as the "electroacoustic model", must be in the form of a rational transfer function, i.e. it must behave as a discrete, infinite impulse response filter.

It should be noted that, because the calculator is digital, analogic-digital and digital-analogic converters are implemented, in particular to sample the analogic signals. Thus, the calculator processes sampled signals, of period Te (in seconds) and frequency Fe=1/Te (in Hertz).

Taken into account the level of the signals involved, a linear approximation of the real system consisted of the electroacoustic and acoustic elements of the passenger compartment may advantageously be performed. In advanced alternative embodiments, it may also be used means intended to avoid the non-linear phenomena of saturation or the like (for example, compression/expansion of the signals, anti-aliasing frequency filters . . . ).

It must also be taken into account that the equations governing the real response of the passenger compartment are partial derivative equations, that is to say that the transfer function representing exactly the real system is of finite dimension (distributed parameter model). Thus, in order to implement the invention, it is necessary to find a compromise to define the electroacoustic model, and the order of the transfer function of said model is chosen with a dimension that is reduced enough no to lead to a too great volume of calculations, but large enough to correctly approximate the model. Such constraint results in that oversampling must be avoided. By way of example, for a maximal frequency of disturbing noise of 120 Hz, a sampling frequency of 500 Hz can be chosen. One of the advantages of choosing a moderated sampling frequency is that it reduces the calculation load of the in-car calculator. It should be noted that, because the loud-speaker amplifier has a far higher sampling frequency (or even, operates with analogic components), it is desirable to place between the output of the calculator and the input of the loud-speaker a low-pass filter operating at the frequency of the loud-speaker amplifier, the cut-off frequency of said filter being constant, so as to reduce the harmonic distortions due to the transition between signals of different sampling periods.

Within the framework of the present invention, a particular form of electroacoustic model has been chosen, which will now be described. However, it will be understood that other forms of electroacoustic model can be used within the framework of the invention, and in particular in the case in which the determinations and calculations of the attenuation system applied to this electroacoustic model would not give a satisfying solution (see herein after the implementation of an optional time of verification of the stability and robustness of the electroacoustic system model and of the RS controller system, with a Youla parameter, during the design phase).

The transfer function of the electroacoustic model that describes the response of the real electroacoustic system can be expressed, between the points u(t) and y(t) of the system, in the absence of any loop. Let $q^{-1}$ be the delay operator of a sampling period, the desired transfer function, in the absence of any loop and noise (the noise that is to be attenuated is not present), is in the form of:

$$\frac{y(t)}{u(t)} = \frac{q^{-d}B(q^{-1})}{A(q^{-1})}$$

where d is the number of delay sampling period of the system, B and A are polynomials in $q^{-1}$, wherein $q^{-1}$ is the delay operator of a sampling period. In particular:

$$B(q^{-1})=b_0+b_1\cdot q^{-1}+ \dots b_{nb}\cdot q^{-nb}$$

$$A(q^{-1})=1+a_1\cdot q^{-1}+ \dots a_{na}\cdot q^{-na}$$

where $b_i$ and $a_i$ are scalar quantities.

Figure 4:
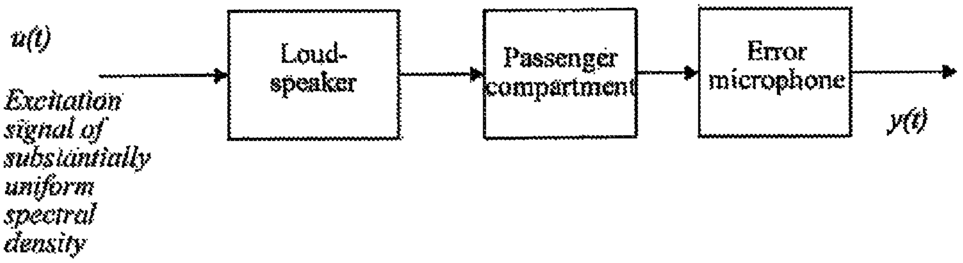
FIG. 4 is a schematic representation of the time of stimulation of the real acoustic system of the car passenger compartment intended to determine and calculate the electroacoustic model that will be use.

The identification is made by stimulating the real system with a signal u(t), whose spectral density is substantially uniform, over the frequency range [0, Fe/2], wherein Fe/2 is the Nyquist frequency. It will be understood that the noise frequency(ies) that are to be attenuated have also to be comprised in the same interval, and Fe is thus chosen as a function of the highest frequency of the noise to be attenuated. Such a stimulating excitation signal may be produced, for example, by a pseudo-random binary sequence (PRBS). Such stimulation, schematically shown in FIG. 4, is performed in the absence of disturbing external noise. All the data of the test u(t) and y(t), during the time of testing the real system (passenger compartment with its electroacoustic components), are recorded so as to be processed in the preferential framework of batch processing.

The algorithms that can be used for identifying the linear systems are numerous. For an overview of the methodologies that can be used, reference can be made, for example, to the work of I.D. Landau: "Commande des systèmes" (2002). After having obtained the rational transfer function, the identification must be validated in order to ensure that the electroacoustic model obtained is correct. Various methods of validation exist according to the emitted hypotheses about the disturbing noise affecting the model (for example, testing the whiteness of the error of prediction). To increase the reliability of the model obtained, it is further possible to validate the model obtained through comparisons between results of simulation on the model obtained and the real system subjected to mono-frequency excitations (comparison of the amplitude and phase of the signals), over a frequency range corresponding to the range of interest for the disturbance rejection.

Preferably, such operation of identification with stimulation is performed for all the configurations of occupation of the passenger compartment of the real model. Such occupation may correspond to positions of passengers, accessories (for example, additional seats), change of acoustic or electronic material, or any other condition liable to modify the electroacoustic response of the passenger compartment. Therefore, it is desirable to carry out identifications for all the configurations of occupation of the passenger compartment, because the multiple models obtained have in fact gain and phase disparities for each frequency.

After having obtained the transfer function of the electroacoustic model, and after having validated it by means of indicated suitable tools, the control law for the rejection of a variable-frequency disturbance will now be synthesized.

The characterization of the level of rejection of the acoustic disturbance that acts on the passenger compartment is made by means of the direct sensitivity function of the closed loop system, named Syp.

Let's suppose that the control law is of the RST type, i.e. a law consisted of three blocks, wherein T=0, and R, S are polynomials such that:

$$R(q^{-1})=r_0+r_1\cdot q^{-1}+ \dots r_{nr}\cdot q^{-nr}$$

$$S(q^{-1})=1+s_1\cdot q^{-1}+ \dots s_{ns}\cdot q^{-ns}$$

The control law is written as follows:

$$u(t) = \frac{R(q^{-1})}{S(q^{-1})} \cdot y(t)$$

Figure 5:
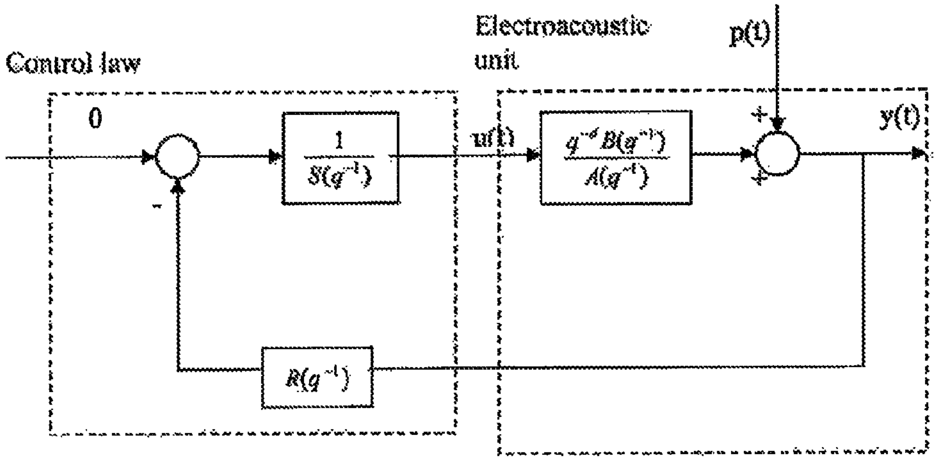
FIG. 5 is a representation of a closed loop system according to the electroacoustic model with a controller of the RST type, referred to as the central controller, with T=0 and in the SISO, single input single output, mono-variable case.

The RST controller is the more general form of implantation of a SISO, single input single output, mono-variable controller. The closed loop system may then be schematized by the block-diagram of FIG. 5, in which $$\frac{q^{-d}B(q^{-1})}{A(q^{-1})}$$

is the transfer function of the above-described electroacoustic model. In this block-diagram, p(t) is the equivalent of the acoustic disturbance that has been deported at the output of system, without loss of generality.

The direct sensitivity function Syp can be defined as the transfer function between the disturbance signal p(t) and the signal y(t) of the microphone. This transfer function describes the response of the closed loop relative to the acoustic disturbance rejection.

In particular, obtaining this function makes is possible to know for any frequency the quality of the disturbance rejection.

It can be shown that this function is written as follows:

$$S_{yp} = \frac{A(q^{-1})S(q^{-1})}{A(q^{-1})S(q^{-1}) + q^{-d}B(q^{-1})R(q^{-1})} \quad (1)$$

Because the object of the control law is to make the disturbance rejection possible at a frequency fpert, the module of Syp has to be low at said frequency, in practice very lower than 0 dB.

Ideally, it would be desirable that Syp is the lowest possible at all the frequencies. Nevertheless, this objective is not reachable because of the Bode-Freudenberg-Looze theorem, which shows that if the system is asymptotically stable in closed loop and is also stable in open loop:

$$\int_0^{0.5.Fe} \log|S_{yp}(e^{-j2\pi f.Fe})|df = 0$$

This means that the sum of the areas between the curve of the sensitivity module and the axis 0 dB, taken with their respective sign, is null. It implies that the disturbance attenuation in a certain frequency region will necessary lead to the disturbance amplification in other frequency regions.

Figure 6:
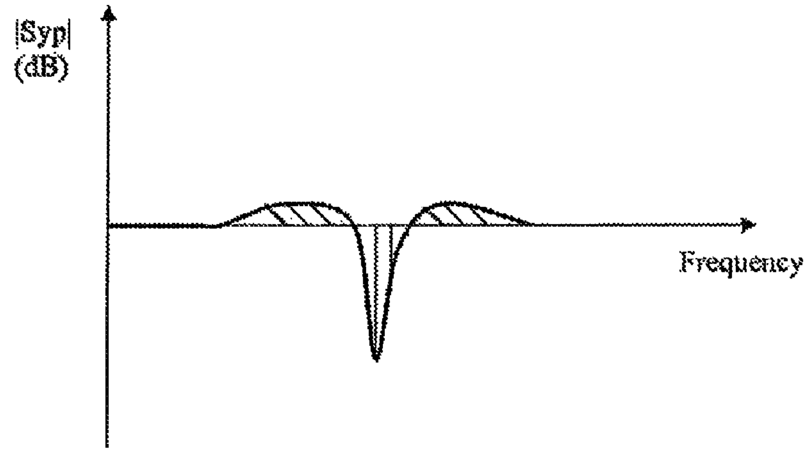
FIG. 6 is an example of a direct sensitivity function and shows that, by applying the Bode-Freudenberg-Looze theorem, the two areas, above and below the axis 0 dB, are equal to each other.

An example of direct sensitivity function is shown in FIG. 6, and the two areas, above and below the axis 0 dB, are equal to each other.

It has been seen hereinabove that the denominator of Syp is written $A(q^{-1})S(q^{-1})+q^{-d}B(q^{-1})R(q^{-1})$, which is a polynomial in $q^{-1}$. The roots of this polynomial form the poles of the closed loop.

The calculation of the coefficients of the polynomials $R(q^{-1})$ and $S(q^{-1})$ can in particular be performed by a pole placement technique. Other calculation techniques exist for synthetizing a linear controller but, preferably, the pole placement technique is preferably used here. It consists in calculating the coefficients R and S by specifying the poles of the closed loop that are the roots of the polynomial P, i.e.:

$$P(q^{-1})=A(q^{-1})S(q^{-1})+q^{-d}B(q^{-1})R(q^{-1}) \quad (2)$$

After these poles have been chosen, P is expressed and the equation (2), which is the Bezout equation, is solved. Details of how to solve the Bezout equation can be found, for example, in above-mentioned the work of I.D. Landau, in pages 151 and 152. It goes through solving a Sylvester system. Moreover, calculation routines according to Matlab® and Scilab® software programs, for solving this equation, are associated with this work. The selection of the poles can be performed according to various strategies. One of these strategies will be explained hereinafter.

The cancellation of the effect of the disturbances p(t) on the output is obtained at the frequencies at which:

$$A(e^{-j2\pi f/Fe})S(e^{-j2\pi f/Fe})=0 \quad (3)$$

Therefore, in order to calculate a controller rejecting a disturbance at the frequency fpert, a part of S is specified a priori, by imposing in the equation (2) that S is factorized by Hs, a polynomial of order 2, for a mono-frequency disturbance, i.e.:

$$Hs=1+h_1\cdot q^{-1}+h_2\cdot q^{-2} \quad (4)$$

If $$h_1 = -2\cos(2\pi \cdot fpert/Fe)$$

$$h_2 = 1,$$

a pair of complex zeros, not damped at the frequency fpert, is introduced.

If $h_2 \neq 1$, a pair of complex zeros, with a non-null damping, can be introduced in S, wherein the damping is chosen as a function of the desired attenuation at a certain frequency.

The Bezout equation to be solved is then:

$$S'(q^{-1})\cdot Hs(q^{-1})\cdot A(q^{-1})+B(q^{-1})R(q^{-1})=P(q^{-1}) \quad (5)$$

In practice, the frequency of the noise to be rejected varies over time, as a function, in particular, of the vehicle crankshaft rotation speed, the block Hs must also vary as a function of said frequency. It then results that a Bezout equation, as follows:

$$S'(q^{-1})\cdot Hs(q^{-1})\cdot A(q^{-1})+B(q^{-1})R(q^{-1})=P(q^{-1}) \quad (6)$$

has to be solved, for each frequency to be rejected. It can be seen that solving this equation, in particular in real time, would lead to a great volume of calculations. Moreover, all the coefficients S and R of the controller are caused to vary during a frequency change. It results in a very heavy algorithm, requiring a significant power of calculation. Thus, even if this simple RS controller solution can be applied, it is preferred to implement another solution that avoids this problem and that minimizes the number of coefficients of the control law varying with the frequency of the disturbance to be rejected.

Therefore, to overcome this problem, it is proposed hereinafter a solution based on the concept of Youla-Kucera parameterization applied to a controller of the RS type.

Figure 7:
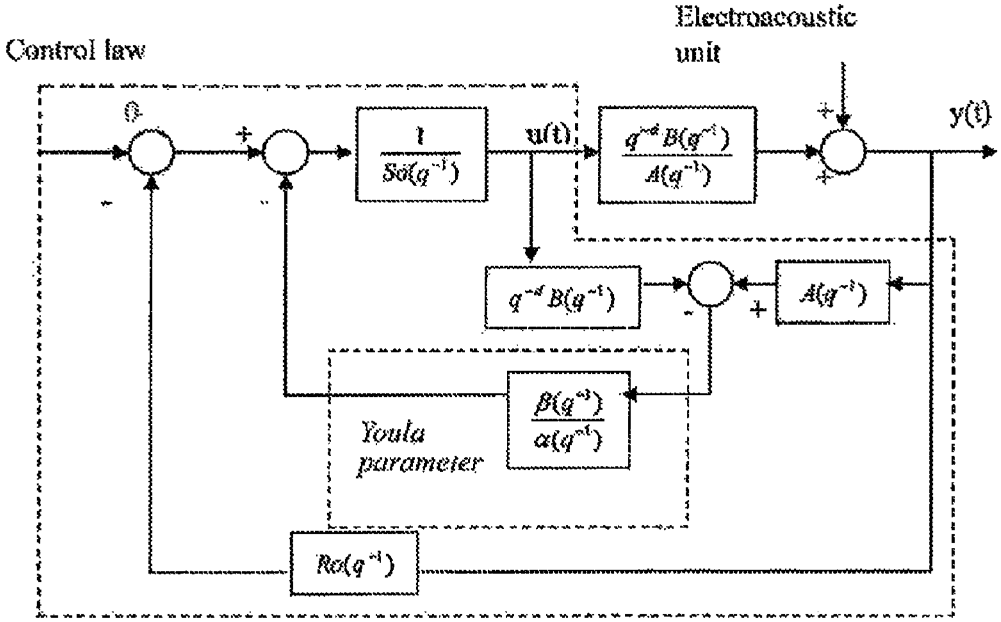
FIG. 7 is a representation of a SISO, single input single output, mono-variable case of control law applied to the electroacoustic model and comprising a central controller of the RS type, to which a Youla parameter has been adjoined.

Such a SISO, single input single output, mono-variable system governed by controller of the RS type, to which the Youla parameter has been adjoined, is schematically shown in FIG. 7.

Such a controller is based on a so-called "central" RS controller consisted of blocks $Ro(q^{-1})$ and $So(q^{-1})$, wherein Ro and So are polynomials in $q^{-1}$.

The Youla parameter is the block $$Q(q^{-1}) = \frac{\beta(q^{-1})}{\alpha(q^{-1})},$$

wherein β and α are polynomials in $q^{-1}$.

As seen hereinabove, the blocks $q^{-d}B(q^{-1})$ and $A(q^{-1})$ are the numerator and denominator of the transfer function of the electroacoustic system to be controlled.

It can be shown that the controller unit thus made and shown in FIG. 7 is equivalent to a controller of the RS type, whose blocks R and S are equal to:

$$R(q^{-1})=Ro(q^{-1})\cdot\alpha(q^{-1})+A(q^{-1})\cdot B(q^{-1})$$

$$S(q^{-1})=So(q^{-1})\cdot\alpha(q^{-1})-q^{-d}B(q^{-1})\cdot\beta(q^{-1}) \quad (7)$$

Now, let's suppose that a central controller has been formed and that it stabilizes the system.

Without Youla parameterization, the characteristic polynomial of the system, Po, as seen above, is written as follows:

$$Po(q^{-1})=A(q^{-1})\cdot So(q^{-1})+q^{-d}B(q^{-1})\cdot Ro(q^{-1}) \quad (8)$$

By providing the central controller with the Youla parameter, the characteristic polynomial of the system is written as follows:

$$P(q^{-1})=A(q^{-1})\cdot(So(q^{-1})\cdot\alpha(q^{-1})-q^{-d}B(q^{-1})\cdot\beta(q^{-1})+q^{-d}B(q^{-1})\cdot(Ro(q^{-1})\cdot\alpha(q^{-1})+A(q^{-1})\cdot\beta(q^{-1}))$$

$$P(q^{-1})=Po(q^{-1})\cdot\alpha(q^{-1})$$

It can be seen that the poles of Q (zeros of a) adjoin the poles of the closed loop, equipped only with the central controller, whose characteristic polynomial is Po.

Moreover, the equation:

$$S(q^{-1})=So(q^{-1})\cdot\alpha(q^{-1})-q^{-d}B(q^{-1})\beta(q^{-1}) \quad (9)$$

can be used to specify the block S with a pre-specification block Hs, that is to say:

$$S'(q^{-1})\cdot Hs(q^{-1})=So(q^{-1})\cdot\alpha(q^{-1})-q^{-d}B(q^{-1})\beta(q^{-1})$$

i.e.:

$$S'(q^{-1})\cdot Hs(q^{-1})+q^{-d}B(q^{-1})\beta(q^{-1})=So(q^{-1})\cdot\alpha(q^{-1}) \quad (10)$$

which is also a Bezout equation, making possible in particular to find β if α and Hs are defined.

Let Sypo be the direct sensitivity function of the closed loop system with the central controller, without Youla parameter.

The direct sensitivity function of the closed loop system with a controller provided with the Youla parameter is written as follows:

$$S_{yp}=S_{ypo}-\frac{q^{-d}B(q^{-1})}{P(q^{-1})}Q(q^{-1}) \quad (11)$$

Therefore, based on a closed loop system comprising a central controller having no vocation to reject a sinusoidal disturbance at a frequency fpert in particular, the Youla parameter can be adjoined to the central controller, which will modify the sensibility function Syp, while keeping the poles of the closed loop provided with the central controller, to which will be adjoined the poles of Q. A notch can then be created in Syp, at the frequency fpert.

For that purpose, Hs and α are calculated in such a manner that the transfer function $$\frac{Hs(q^{-1})}{\alpha(q^{-1})}$$

results from the discretization of a continuous block of the second order by the Tustin method, with "pre-warping":

$$\frac{\frac{s^2}{(2\pi\cdot fpert)^2}+\frac{2\cdot\varsigma_1\cdot s}{(2\pi\cdot fpert)}+1}{\frac{s^2}{(2\pi\cdot fpert)^2}+\frac{2\cdot\varsigma_2\cdot s}{(2\pi\cdot fpert)}+1}$$

Hs and α are polynomials in $q^{-1}$ of degree 2, and $\varsigma_1$, $\varsigma_2$ are damping coefficients of a transfer function of the second order.

Moreover, the operation of discretization of the continuous transfer function (in s) can be performed by means of calculation routines that can be found, for example, in the calculation software programs dedicated to the automatic control engineering. In the Matlab® case, it is the function "c2d".

It can be shown that the attenuation M at the frequency fpert is given by:

$$M=20\log\left(\frac{\varsigma_1}{\varsigma_2}\right), \text{ with } \varsigma_1<\varsigma_2 \quad (12)$$

Further, it is necessary that $\varsigma_1<1$.

Moreover, for an equal ratio of $$\frac{\varsigma_1}{\varsigma_2},$$

it is shown that the notch in the sensitivity function Syp is all the more wide that $\varsigma_2$ is great. But, the more this notch is wide, the more |Syp| is deformed at the frequencies other than fpert (a consequence of the Bode-Freudenberg-Looze theorem). Therefore, a compromise is determined by choosing $\varsigma_1$, $\varsigma_2$ n such a way to create a sufficiently wide attenuation around fpert, without causing a too significant rise of |Syp| at the other frequencies. Typical values of the damping factors are: $\varsigma_1$=0.01 $\varsigma_2$=0.1. These values can constitute a start point for a refining.

Thereafter, β can be calculated by solving the Bezout equation (10).

It is shown that this choice of Hs and α creates a notch in the sensitivity function Syp, while having an almost-negligible effect at the other frequencies with respect to Sypo, even if the Bode-Freudenberg-Looze theorem applies, which causes a rise of the module of Syp with respect to Sypo at frequencies other than fpert.

Such rise of Syp can reduce the robustness of the closed loop that can be measured by the module margin (distance to the point −1 from the frequency position of the open loop corrected in the Nyquist plane) equal to the inverse of the maximum of |Syp| over the frequency range [0; Fe/2].

The main advantage of using the Youla parameterization lies in the fact that α is of order 2:

$$\alpha(q^{-1})=1+a_1\cdot q^{-1}+\alpha_2\cdot q^{-2} \quad (13)$$

Moreover, β of order 1:

$$\beta(q^{-1})=\beta_1\cdot q^{-1}+\beta_2\cdot q^{-2} \quad (14)$$

Therefore, with the proposed system of controller of RS type, to which the Youla parameter is adjoined, the number of parameters varying as a function of the frequency of the disturbing noise to be rejected in the control law is only of 4. The calculation of these parameters as a function of the frequency f of the disturbance to be rejected can be performed beforehand, out-of-line, by solving the Bezout equation (10), during the design phase of the control law, wherein the parameters can be memorized in tables in the in-car programmable calculator and called, in real time, as a function of the frequency to be rejected.

Figure 8:
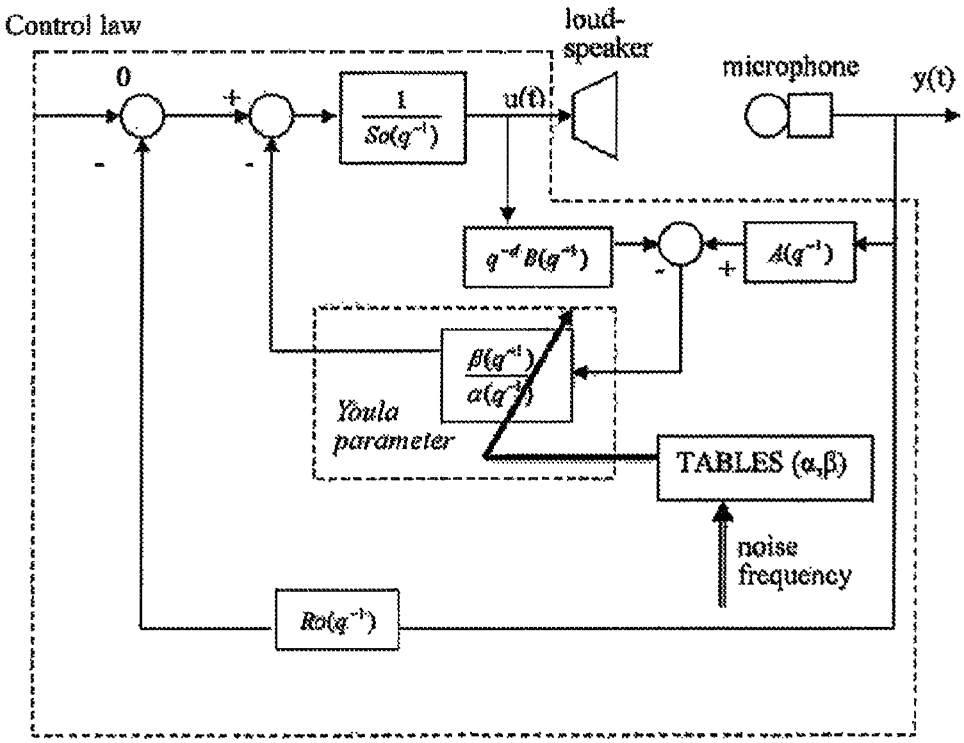
FIG. 8 is a representation of the complete diagram of a control law with a central controller of the RS type, to which a Youla parameter has been adjoined, and calculated in real time in use phase, for noise attenuation in the passenger compartment.

FIG. 8 shows the complete diagram of the control law (central RS controller+Youla parameter Q).

To perform the synthesis of the controller, it is preferable to use an electroacoustic model that can be qualified as median, i.e. a model corresponding to an intermediate level of occupation of the passenger compartment, among the electroacoustic models corresponding to the different configurations of occupation of the passenger compartment.

For the synthesis of the central controller, the purpose is preferably to ensure maximum margins without a particular objective of disturbance rejection. This can be obtained, for example, by means of a pole placement technique, and, if necessary, it can be referred to the above-mentioned work of I.D. Landau, in particular all the Chapter 3. More precisely, it can be proceeded as explained hereinafter. It is chosen to perform the closed loop pole placement by placing n dominant poles of the closed loop on the n poles of the system to be controlled, i.e. the roots of $A(q^{-1})$, wherein n is the degree of the polynomial A. There is no pre-specification of the block So because the purpose is not to reject a disturbance by means of the central controller alone. By performing this operation, the central controller does not reject at all the disturbances p(t), but ensures a maximum robustness.

A certain number of auxiliary "high-frequency" poles, whose value is comprised between 0.05 and 0.5 in the complex plane (in the case in which there is no over-sampling) can also be placed. It should be borne in mind that a sampled system is stable if all its poles are strictly comprised in the unit circle in the complex plane. These auxiliary poles have for role to increase the robustness of the control law, during the adjoining of the Youla parameter.

After the poles of the closed loop, i.e. the roots of $Po(q^{-1})$, have been chosen, $Po(q^{-1})$ in expressed, which is a polynomial in $q^{-1}$, of degree n+m. Thereafter, the Bezout equation is solved using the above-mentioned routines:

$$So(q^{-1})\cdot A(q^{-1})+q^{-d}B(q^{-1})\cdot R'o(q^{-1})=Po(q^{-1}) \quad (15)$$

wherein $S_0$ and $R'_0$ are unknown.

The central controller has therefore been determined and calculated.

The coefficients of the Youla parameter Q (i.e. α and β), which are the only varying polynomials of the control law as a function of the frequency of the disturbance to be rejected, are then calculated.

For each of the frequencies fpert of the disturbance to be rejected, the damping factors $\varsigma_1$, $\varsigma_2$ of the equation (12) are chosen, in such a manner to adjust the depth of attenuation of Syp at said frequency, as well as the width of the notch (bandwidth) at the frequency fpert in Syp, while keeping a sufficient robustness, that can be measured by the above-described module margin (maximum of Syp). It can be set, for example, as an objective, a module margin of 0.7, which corresponds to a high level of robustness of the closed loop, a robustness that will ensure the stability of the active control system with variations of the passenger compartment configuration.

It is known that a closed-loop control is all the more robust that the poles of the closed loop are close to the system to be controlled. Such condition is fully satisfied by the choice of the pole placement at the time of the central controller synthesis.

The polynomials $Hs(q^{-1})$ and $\alpha(q^{-1})$ are calculated as explained above, by discretization of a transfer function of the second order and the Bezout equation (10) is solved so as to determine $\beta(q^{-1})$.

Preferably, this calculation providing the determination of $\alpha(q^{-1})$ and $\beta(q^{-1})$ as a function of fpert is performed over the whole frequency range in which it is desired to carry out a disturbance rejection. α and β can for example be calculated for frequencies varying by increments of 2 Hz, over a range comprised between 30 and 120 Hz.

In addition to the electroacoustic model(s) and the central RS controller model obtained, all the coefficients of the polynomials $\alpha(q^{-1})$ and $\beta(q^{-1})$ as a function of fpert are memorized in a memory, a table for these latter, of the calculator. The tables make it possible to find the data that will have to be used in real time as a function of the current conditions, in particular the current frequency of the noise to be attenuated, and possibly the current configuration of occupation of the passenger compartment.

Therefore, the control law (RS controller+Youla parameter) is then synthetized. It is possible, in an optional time of the design phase, to verify that it is provided with stability and a correct level of robustness (module margin>0.5), with simulation of the closed loop system and disturbance rejection over all the frequency range, for all the configurations of occupation of the passenger compartment, using the electroacoustic models identified in the various configurations. If it is not the case, the design of the control law is modified by acting on the coefficients $\varsigma_1$, $\varsigma_2$ (depth and frequency width of the rejection). if it is still not sufficient, it may be tried to take as electroacoustic model another model among those obtained for the various configurations of passenger compartment, or also to act on the placement of the auxiliary poles of the closed loop (high-frequency poles).

These preliminary times of design and synthesis need significant calculations, so that they are preferably batch performed. Once the synthesis is performed, the models obtained can be applied in real time to the calculator to obtain the noise attenuation in the passenger compartment.

When the calculator operates in real time, as shown in FIG. 8, the memorized data, in particular the coefficients of the polynomials $\alpha(q^{-1})$ and $\beta(q^{-1})$ for the Youla parameter, are called as a function of the information about the current frequency of the noise to be rejected, coming for example indirectly from a tachometer measurement on the crankshaft. For values of current frequency that do not correspond directly to the frequencies of the inputs of the table (a current frequency between two frequencies of calculation of the table values), an estimation of the coefficients of the polynomials $\alpha(q^{-1})$ and $\beta(q^{-1})$ may be made, by performing an interpolation between calculated coefficients for two known frequency values or more. In the latter case, it is preferable that the frequency mesh is not too large between the frequencies used for the coefficient calculations, a mesh with increments of 2 Hz being generally suitable.

To summarize the above-mentioned example, it can be considered that the invention relates to a real-time active method for attenuating, through feedback, a narrow-band noise, essentially mono-frequency at least one determined frequency, in a vehicle passenger compartment, by emitting a sound through at least one transducer, typically a loudspeaker, controlled by a signal u(t) generated by a programmable calculator, as a function of a signal of acoustic measurement y(t), performed by at least one acoustic sensor, typically a microphone, wherein, in a first phase of design, the electroacoustic response of the unit formed by the passenger compartment, the transducer and the sensor, is modelled by an electroacoustic model as an electroacoustic transfer function that is determined and calculated, a control law being then determined and calculated from an global model of the system in which the control law is applied to the electroacoustic transfer function whose output additionally receives a noise signal p(t) to give the signal y(t) in said design phase, said control law making it possible to produce the signal u(t) as a function of the acoustic measurements y(t), and in a second phase of use, said calculated control law is used in the calculator to produce the signal u(t) then sent to the transducer as a function of the signal y(t) received from the sensor for attenuating said noise.

More particularly, in the design phase:

a)—in a first time, it is used as an electroacoustic model a discrete rational electroacoustic transfer function, and said electroacoustic model is determined and calculated by acoustic excitation of the passenger compartment by the transducer and acoustic measurements by the sensor, then application of a linear system identification process with the measures and the model of the transfer function, b)—in a second time, a control law is implemented, which comprises a so-called "central" RS controller of two blocks $$\frac{1}{So(q^{-1})}$$

and $Ro(q^{-1})$, in the central controller, the block $$\frac{1}{So(q^{-1})}$$

producing the signal u(t) and receiving as an input the inverted output signal of the block $Ro(q^{-1})$, said block $Ro(q^{-1})$ receiving as an input the signal y(t) corresponding to the sum of the noise p(t) and of the output of the electroacoustic transfer function of the electroacoustic model, and the central controller is determined and calculated, c)—in a third time, a Youla parameter in introduced into the control law, in the form of a Youla block $Q(q^{-1})$ adjoined to the central RS controller, said Youla block $Q(q^{-1})$ receiving a noise estimation obtained by calculation from the signals u(t) and y (t) and as a function of the electroacoustic transfer function and the output signal of said Youla block $Q(q^{-1})$ being subtracted from the inverted signal of $Ro(q^{-1})$ sent to the input of the block $$\frac{1}{So(q^{-1})}$$

of the central RS controller, and the Youla parameter $Q(q^{-1})$ in the control law comprising the central controller with which is associated the Youla parameter is determined and calculated for at least one noise frequency p(t), including at least the determined frequency of the noise to be attenuated, and in the use phase, in real time:

- the current frequency of the noise to be attenuated is determined,
- the calculator is caused to calculate the control law, comprising the RS controller with the Youla parameter, using as that which has been calculated for a determined frequency corresponding to the current frequency of the noise to be attenuated.

Up to now, it has been presented a simple implementation with a passenger compartment provided with a single one microphone and one loud-speaker, or a group of loud-speakers, all of them being excited by the same signal.

But the fact is that the noise reduction/the silence that can be obtained by an active control process is very localized in space. In the above-mentioned article "A review of active noise and vibration control in road vehicles", Eliott indicates that the silence zone around the error microphone does not exceed one tenth of the wavelength of the noise to be rejected, i.e. about 110 cm for a noise of 30 Hz, 55 cm for a noise of 60 Hz, 28 cm for a noise of 120 Hz, at ambient temperature.

Thus, it can be seen that it is not possible to obtain a uniform noise reduction with a single one microphone in a rather spacious car passenger compartment, and that it is necessary to multiply the number of error microphones and to distribute them in the passenger compartment to increase the space in with there is noise reduction.

In the following, in order to generalize the explanations, it will be referred to the case in which the passenger compartment is equipped with several microphones and several loud-speakers (or groups of loud-speakers). Such generalisation permits to understand the more specific applications with particular numbers of loud-speaker(s) and microphone(s).

A first solution consists in using the control diagram previously established for a single one microphone, in order to perform a one-to-one loud-speaker-microphone looping. However, such solution might give very bad results, or even instability. Indeed, a given loud-speaker of a modeled system will have an effect on all the microphones of the passenger compartment, even those which are not included in its own modeled system.

Another more global solution is thus proposed, considered from an automatic control engineering point of view. Here, with several microphones, we are in presence of a MIMO, multi-inputs-multi-outputs-variables problem, i.e. with several inputs and several outputs coupled to each other.

Figure 9:
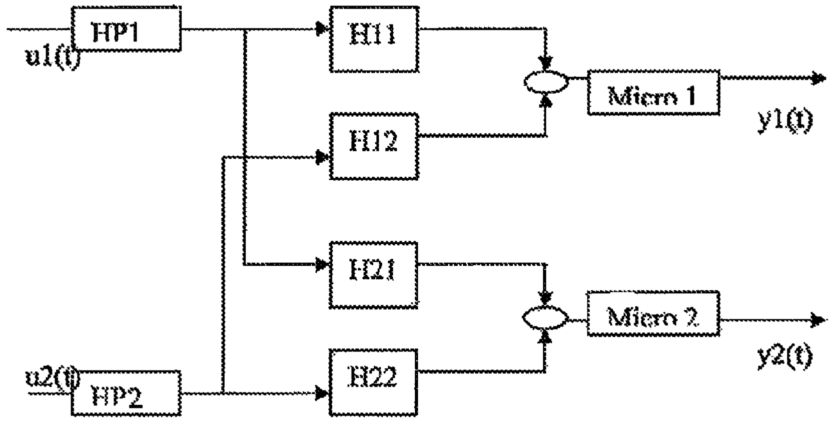
FIG. 9 is a representation of a diagram of the transfer on a system of 2 loud-speakers and two microphones, and thus in the MIMO, multi-inputs-multi-outputs-variables case.

By way of example, FIG. 9 shows a diagram of the electroacoustic transfer on a system 2*2 (2 loud-speakers, 2 microphones). In this example, the microphone 1 is sensitive to the acoustic effects of the loud-speaker 1 (HP1) and of the loud-speaker 2 (HP2). Also, the microphone 2 is sensitive to the acoustic effects of the loud-speaker 2 (HP2) and of the loud-speaker 1 (HP1). Such system, given by way of example, can be modeled by the following matrix of transfer functions:

$$\begin{bmatrix} y1(t) \\ y2(t) \end{bmatrix} = \begin{bmatrix} L11 & L12 \\ L21 & L22 \end{bmatrix} \cdot \begin{bmatrix} u1(t) \\ u2(t) \end{bmatrix} \tag{16}$$

or, still in the case (2*2):

$$\begin{bmatrix} y1(t) \\ y2(t) \end{bmatrix} = \begin{bmatrix} \frac{B11(q^{-1})}{A11(q^{-1})} & \frac{B12(q^{-1})}{A12(q^{-1})} \\ \frac{B21(q^{-1})}{A21(q^{-1})} & \frac{B22(q^{-1})}{A22(q^{-1})} \end{bmatrix} \cdot \begin{bmatrix} u1(t) \\ u2(t) \end{bmatrix} \tag{17}$$

The representation of a MIMO, multi-inputs-multi-outputs-variables system by a transfer function is indeed not much convenient, and a state representation is preferred, which is a universal representation of the linear systems (whether they are MIMO, multi-inputs-multi-outputs-variables or not).

Let:

nu be the number of inputs of the system (i.e. the number of loud-speakers or groups of loud-speakers connected to each other);

ny be the number of outputs of the system (i.e. the number of microphones);

n be the order of the system.

In the following, in order to simplify the explanations, it considered that nu=ny, but it is not restrictive, and the following can also apply to the case nu>ny.

The state representation of the electroacoustic system (of the passenger compartment) can be written as a recurrence equation referred to as "state equation":

$$X(t+Te)=G\cdot X(t)+H\cdot U(t)$$

$$Y(t)=W\cdot X(t) \quad (18)$$

with:
X: state vector of the system of dimension (n*1)
U: vector of the inputs of the system of dimension (nu*1)
Y: vector of the outputs of dimension (ny*1)
and:
G: a matrix referred to as "evolution matrix" of dimension (n*n)
H: the input matrix of the system of dimension (n*nu)
W: the output matrix of the system of dimension (ny*n).

The coefficients of the matrices G, H, W define the MIMO, multi-inputs-multi-outputs-variables linear system.

Let's state that X (t) corresponds to the vector X at the instant t and X (t+Te) corresponds to the vector X at the instant t+Te (i.e. a sampling period after X(t)).

The control law is based on this state representation, and hence, as for the SISO, single input single output, mono-variable case, the model of the electroacoustic system to be controlled (electroacoustic model of the passenger compartment), i.e. the coefficients of the matrices G, H, W, must be determined.

Figure 10:
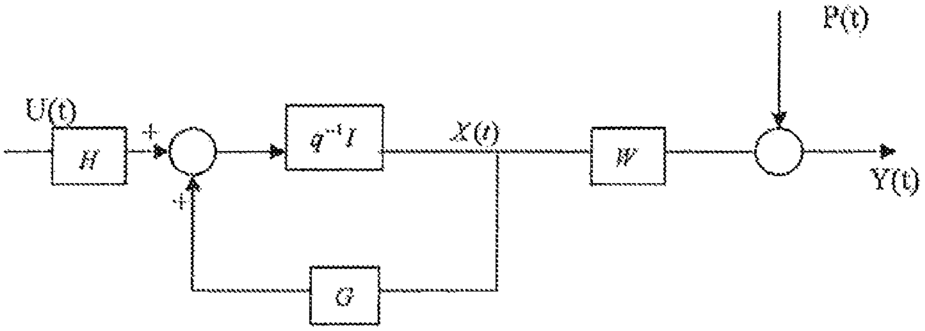
FIG. 10 is a representation as a block-diagram of the system to be controlled, i.e. the electroacoustic model of the passenger compartment, in the MIMO, multi-inputs-multi-outputs-variables case.

FIG. 10 shows a block-diagram of the electroacoustic model of the passenger compartment in the MIMO, multi-inputs-multi-outputs-variables case, where I corresponds to the identity matrix, and which corresponds to the formula (18). By analogy with the SISO, single input single output, mono-variable case, P(t) is the vector of the disturbances on the outputs, i.e.:

$$P(t)=\begin{pmatrix} p_1(t) \\ \vdots \\ p_{ny}(t) \end{pmatrix}$$

in $p_1 \ldots p_{ny}$, wherein $p_i$ is the disturbance on the output i.

As for the SISO, single input single output, mono-variable case, the coefficients of the model of the electroacoustic system to be controlled are obtained by an identification procedure during the design phase, i.e. by stimulation of the real electroacoustic system with noises having substantially uniform spectral density, the nu loud-speakers being excited by signals that are de-correlated from each other.

Then, the input (microphone measurements) and output (signals for the loud-speakers) data are memorized in a calculator and are processed therein so as to obtain a state representation of said system, using this time identification algorithms that are dedicated to MIMO, multi-inputs-multi-outputs-variables systems. These algorithms are, for example, provided in toolboxes of software programs specialized in the field of the automatic control engineering such as, for example, Matlab®. Reference can also be advantageously made to the work of L. LJUNG, "System identification Theory for the user", Prentice Hall, Englewood Cliffs, N.S, 1987, the algorithms presented in this work having giving rise to a toolbox dedicated to the identification in the Matlab® software program. It is the same thing for the algorithms for the validation of the model obtained for the electroacoustic system to be controlled.

Another possible embodiment consists in performing an identification of the nu*ny transfer function, one after the other, with the SISO, single input single output, mono-variable identification tools, and by stimulating the loud-speaker one after the other, and thereafter aggregating the nu*ny models into a single, MIMO, multi-inputs-multi-outputs-variables one. Such aggregation can be performed, for example, by means of the innovative Least Mean Square method, the algorithm being described in the work of Ph. de Larminat: "Automatic appliquée", Hermès 2007.

As for the SISO, single input single output, mono-variable case, it is desirable to carry out an identification for each of the configurations of the passenger compartment and to take as the electroacoustic system model that is kept for the following of the design phase a model that can be qualified as "median".

Once an input-output model of the electroacoustic system has been obtained as a state representation and the model has been validated, the control law can then be determined and calculated. Now, a control law has thus to be synthetized, which permits to reject at each of the microphones an acoustic disturbance of frequency fpert, wherein said frequency fpert can change over time.

For that purpose, the central controller concept and the Youla parameter concept of the SISO, single input single output, mono-variable case are generalized to the MIMO, multi-inputs-multi-outputs-variables case.

It is considered that the electroacoustic system is described by the state representation (18). It can be shown that the central controller in the MIMO, multi-inputs-multi-outputs-variables case is in the form: state observer+feedback on the estimated state, as:

$$\hat{X}(t+Te)=G\cdot\hat{X}(t)+H\cdot U(t)+Kf\cdot(Y(t)-W\cdot\hat{X}(t)) \quad (19)$$

where:
$\hat{X}$ is the state vector of the observer of dimension (n*1)
Kf is the gain of the observer of dimension (n*ny).
Thus:

$$\hat{X}(t+Te)=(G\cdot Kf\cdot W)\cdot\hat{X}(t)+H\cdot U(k)+Kf\cdot(Y(t)) \quad (20)$$

and the control is written as follows:

$$U(t)=-Kc\cdot\hat{X}(t) \quad (21)$$

wherein Kc is the vector of feedback on the estimated state of the system, of dimension (nu*n).

It can advantageously be referred to the work "Robustesse et commande optimale" (Alazard et al., editions CEPADUES, 1999, pages 224 and 225).

Figure 11:
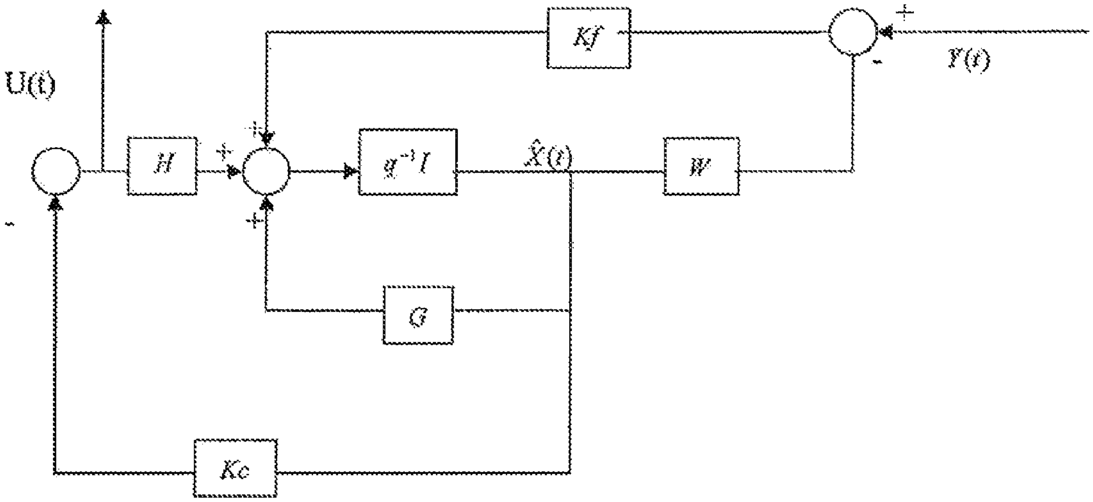
FIG. 11 is a representation as a block-diagram of the central controller, in the MIMO, multi-inputs-multi-outputs-variables case.
Figure 12:
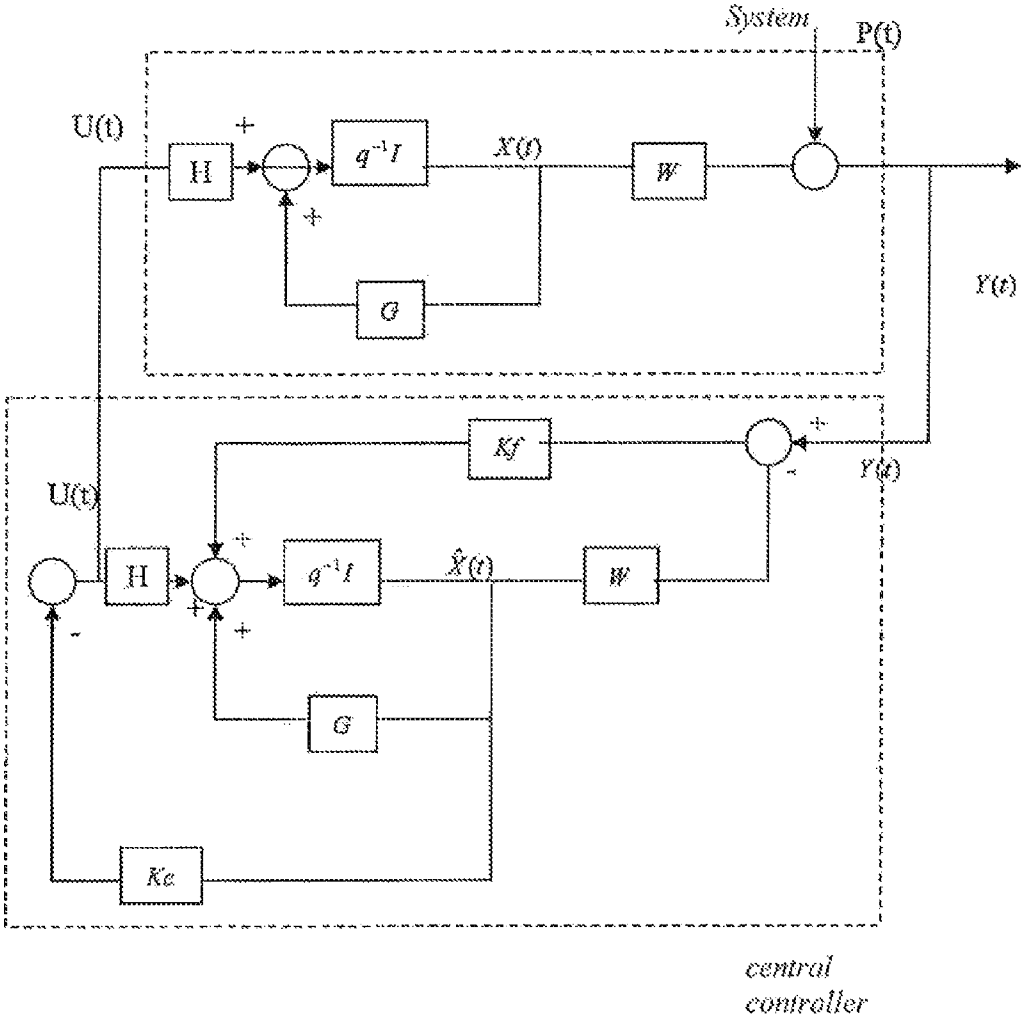
FIG. 12 is a representation as a block-diagram of the central controller applied to the electroacoustic model of the passenger compartment, in the MIMO, multi-inputs-multi-outputs variable case.

In correspondence to these formulas, FIG. 11 shows the block-diagram of the central controller and FIG. 12 shows the block-diagram of the central controller applied to the electroacoustic model of the passenger compartment, still in the MIMO, multi-inputs-multi-outputs-variables case. This latter correction structure is a conventional structure in automatic control engineering. In accordance with a principle known as "separation principle", the poles of the closed loop are formed of the eigenvalues of G−Kf·W and the eigenvalues of G−H·Kc, i.e.:

eig(G−Kf·W)∪eig(G−H·Kc).

eig(G−Kf·W) are designated filtering poles, and
eig(G−H·Kc) are designated control poles.
wherein eig( ) designates the eigenvalues.

Therefore, the poles placement of the closed loop provided with the central controller can be performed by choosing the coefficients Kf and Kc, which are the setting parameters of this control structure. The number of poles to be place is 2*n.

This estimated set observer and feedback of state is thus chosen as the central controller. In the SISO, single input single output, mono-variable case, it has been shown that, if n poles of the closed loop are placed on n poles of the electroacoustic system (i.e. the roots of the polynomials $A(q^{-1})$), a central controller is obtained that does not reject specifically the disturbances, but having a maximum robustness.

In the MIMO, multi-inputs-multi-outputs-variables case, the purpose is also that the central controller has the maximum robustness, without particular objective of disturbance rejection. Therefore, the filtering poles are chosen equal to the poles of the system to be controlled. It is thus required that Kf·W=0.

The most trivial solution is:

$$Kf=0_{n*ny} \tag{22}$$

Thus, the equation of the central controller becomes:

$$\hat{X}(t+Te)=(G)\cdot\hat{X}(t)+H\cdot U(t) \tag{23}$$

It remains n other poles to be placed (the control poles eig(G−H·Kc)). Following what have been done for the SISO, single input single output, mono-variable controller, these poles will be chosen as a set of high-frequency poles intended to ensure the robustness of the control law. It should be noted that, because it is a MIMO, multi-inputs-multi-outputs-variables situation, the number of coefficients of Kc (nu*n) is greater than the number of poles remaining to be placed (n), and thus these degrees of freedom can be used advantageously to perform a eigenstructure placement (choosing not only eigenvalues by also eigenvectors of (G−H·Kc).

Another way to proceed to calculate Kc consists in performing a linear-quadratic (LQ) optimization, regarding to which the literature is very extensive. Reference can for example be made to the work "Robustesse et commande optimale", editions CEPADUES, 1999, pages 69-79. It is also possible to perform, for calculating the coefficients of the matrix Kc, what Ph. de Larminat calls a B-type LQ optimization, i.e. an optimization based on a horizon Tc. The detail of this B-type LQ optimization can be found in the work of Ph. de Larminat: "Automatic appliquée", Hermès 2007. In particular, associated with this work is a calculation routine for the Matlab® software program, for calculating the coefficients of Kc according to the B-type LQ optimization.

The central controller being thus determined and calculated, the way to determine and calculate the Youla parameter that is associated with the central controller for providing the control law in the MIMO, multi-inputs-multi-outputs-variables case will now be described. The objective is still to reject sinusoidal disturbance of known frequency fpert, here at the level of each microphone, by causing only the coefficients of the Youla parameter to vary when fpert varies.

Figure 13:
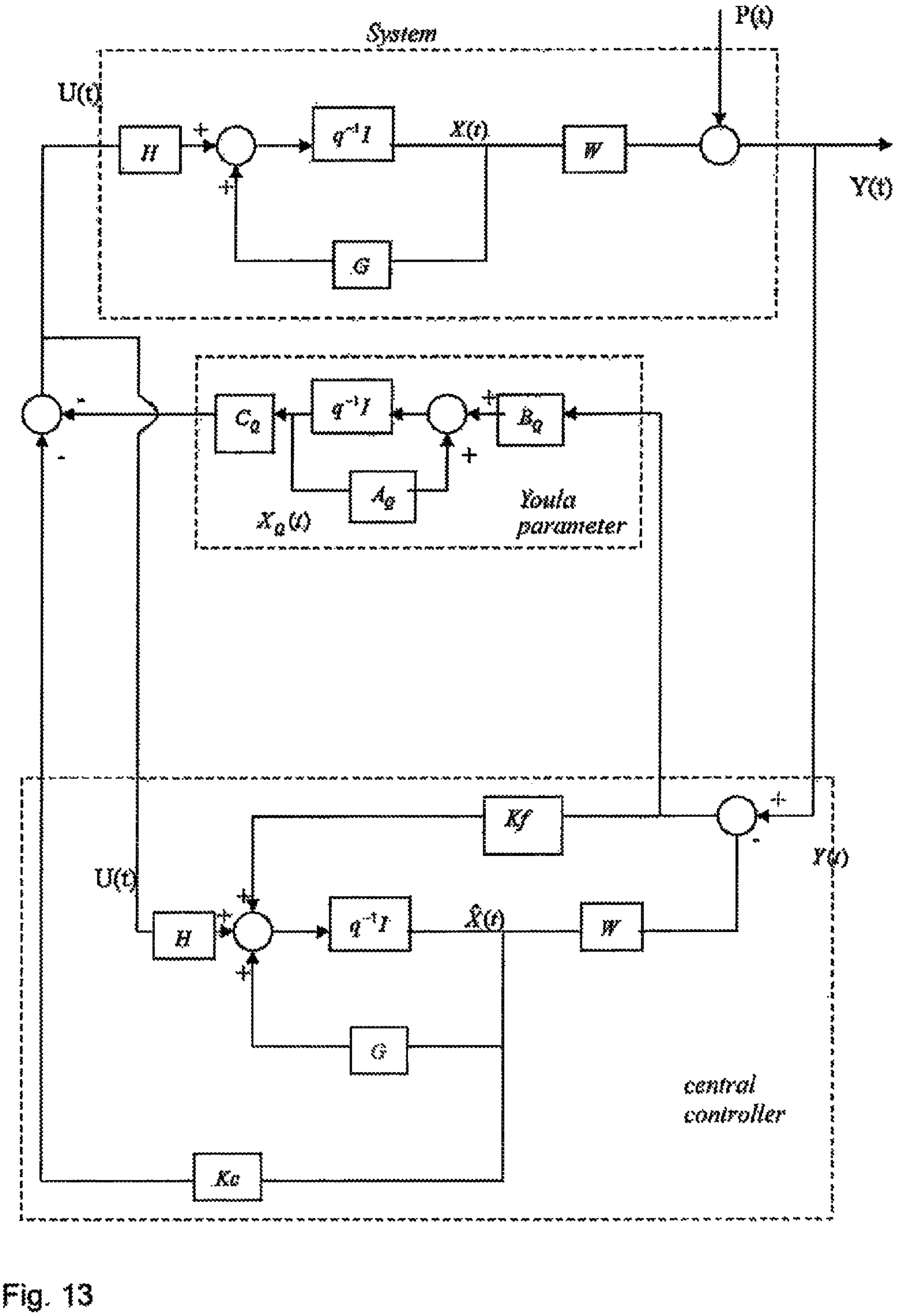
FIG. 13 is a representation as a block-diagram of the control law, central controller+Youla parameter, applied to the electroacoustic model of the passenger compartment, in the MIMO, multi-inputs-multi-outputs-variables case.

It can be shown that the Youla parameter is associated to the central controller to form the control law, as shown in FIG. 13. The explanation of the diagram of FIG. 13 can be found, for example, in the work "Robustesse et commande optimale", editions CEPADUES, 1999, pages 224-225.

In the control law as symbolically shown in FIG. 13, the Youla parameter Q is itself a MIMO, multi-inputs-multi-outputs-variables block, whose state representation can be written as follow:

$$X_Q(t+Te)=A_QX_Q(t)+B_Q(Y(t)-W\cdot\hat{X}(t)) \tag{24}$$

where $X_Q$ is the state vector of the Youla parameter.

The control law of the central controller provided with the Youla parameter is then written by:

$$U(t)=-K_c\cdot\hat{X}(t)-C_Q\cdot X_Q(t) \tag{25}$$

wherein this control law corresponds to a state feedback of the observer associated with a state feedback of the Youla parameter.

The way to determine the parameters of Q so as to ensure a rejection of disturbances of known frequency will now be described.

In the SISO, single input single output, mono-variable case, a transfer function $$\frac{HS(q^{-1})}{\alpha(q^{-1})}$$

was calculated by discretization of a continuous transfer function of the second order and α was then the denominator of the Youla parameter and Hs was used in a Bezout equation making it possible to find β, the numerator of the Youla coefficient.

In the MIMO, multi-inputs-multi-outputs-variables case, a non-controllable disturbance model is applied to each output i:

For each output i, this non-controllable disturbance model is written as follows:

$$\hat{X}_2(t+Te)=G_{2i}\hat{X}_{2i}(t)$$

$$Z_{2i}(t)=W_{2i}\hat{X}_{2i}(t) \tag{26}$$

where:

$\hat{X}_{2i}$ is the state vector of the model of disturbance i (dimension 2*1)

$Z_{2i}$ is the additive disturbance of the output i (dimension 1*1) with:

$$G_{2i}=\begin{bmatrix} -hs_{1i} & 1 \\ -hs_{2i} & 0 \end{bmatrix} \tag{27}$$

and $$W_{2i}=[1\quad 0] \tag{28}$$

It should be noted that the choice of the form of $G_{2i}$, $W_{2i}$ is not unique. A canonical representation of observability has been adopted here.

$hs_{1i}$ and $hs_{2i}$ are deducted from the numerator of a transfer function $$\frac{HS_i(q^{-1})}{\alpha_i(q^{-1})}$$

resulting from the discretization of a continuous transfer function of second order, identical to that which is used in the SISO, single input single output, mono-variable case:

$$\frac{\dfrac{s^2}{(2\pi\cdot fpert)^2}+\dfrac{2\cdot\varsigma_{1i}\cdot s}{(2\pi\cdot fpert)}+1}{\dfrac{s^2}{(2\pi\cdot fpert)^2}+\dfrac{2\cdot\varsigma_{2i}\cdot s}{(2\pi\cdot fpert)}+1} \tag{28a}$$

with:

$$Hs_i(q^{-1})=h_{0i}+h_{1i}\cdot q^{-1}+h_{2i}\cdot q^{-2}$$

-continued $$hs_{1i}=\frac{h_{1i}}{h_{0i}} \text{ and } hs_{2i}=\frac{h_{2i}}{h_{0i}}$$

The discretization of the continuous transfer function can be performed, for example, by means of the calculation routine "c2d" of the Matlab® software program.

The state equation of an observer, increased by the disturbance models on the outputs, can then be written, as follows:

$$\hat{X}(t+Te)=G\cdot X(t)+H\cdot U(t)$$

$$\hat{X}_2(t+Te)=G_2\cdot\hat{X}_2(t)+Kf_2\cdot(Y-W\cdot\hat{X}(t)-W_2\cdot\hat{X}_2(t)) \quad (29)$$

with:

$$U(t)=-Kc\cdot\hat{X}(t)-Kc_2\cdot\hat{X}_2 \quad (30)$$

where:

$Kf_1$ is of dimension (2*ny,ny)

$Kc_1$ is of dimension (nu, 2*ny)

and with:

$$G_2=\begin{pmatrix} G_{21} & 0 & \ldots & 0 \\ 0 & G_{22} & & 0 \\ \vdots & & & \vdots \\ 0 & \ldots & & G_{2ny} \end{pmatrix}, \quad (31)$$

a matrix of dimension $(2ny*2ny)$ $$\hat{X}_2(t)=\begin{pmatrix} \hat{X}_{21}(t) \\ \hat{X}_{22}(t) \\ \vdots \\ \hat{X}_{22}(t) \end{pmatrix}, \quad (32)$$

a vector of dimension $(2ny*1)$

This vector being the state vector of the non-controllable model.

$$W_2=\begin{pmatrix} W_{21} & 0 & \ldots & 0 \\ 0 & W_{22} & & 0 \\ \vdots & & & \vdots \\ 0 & 0 & \ldots & W_{2ny} \end{pmatrix}, \quad (33)$$

a matrix of dimension $(ny*2ny)$

The equation (29) of the observer can also be written as follows:

$$\hat{X}(t+Te)=G\cdot\hat{X}(t)+H\cdot U(t)$$

$$X_2(t+Te)=(G_2-Kf_2\cdot W_2)\cdot\hat{X}_2(t)+Kf_2\cdot(Y-W\cdot\hat{X}(t)) \quad (34)$$

The coefficients of $Kf_2$ have now to be chosen, so as to place the poles of this part of the increased observer.

By choosing for poles the 2ny roots of the denominators $\alpha_i(q^{-1})$, what is done in the mono-variable case is generalized to the multi-variable case.

More precisely, $eig(G_{2i}-Kf_{2i}\cdot W_2)$ is chosen equal to the roots of the above-mentioned polynomials $\alpha_i(q^{-1})$, such polynomials resulting, as described above, from the discretization of a continuous transfer function of the second order.

The calculation of $Kf_{2i}$ as a function of $G_{2i}$, $W_{2i}$ and $\alpha_i(q^{-1})$, is a conventional pole placement operation. To execute this operation, it is for example possible to use the Matlab® routine dedicated to this operation, whose name is "PLACE".

Under this latter condition, the matrix $Kf_{2i}$ is diagonal by blocks, i.e.:

$$Kf_2=\begin{pmatrix} Kf_{21} & 0 & \ldots & 0 \\ 0 & Kf_{22} & & \\ & & & \vdots \\ 0 & & \ldots & Kf_{2ny} \end{pmatrix} \quad (35)$$

It remains to choose $Kc_2$ of dimension (nu*2ny). This choice is not free if it is desired to obtain an asymptotic rejection of the output disturbances.

$Kc_2$ must satisfy the so-called "asymptotic rejection" equations, which are as follows:

$$Kc_2=Ga+Kc\cdot Ta \quad (36)$$

with:

$$Ta\cdot G_2-G\cdot Ta-H\cdot Ga=0$$

$$W\cdot Ta-W_2=0 \quad (37)$$

The explanation of the equations (36) and (37) can be found in the work of Ph. de Larminat: "Automatic appliquée", Hermès 2007, pages 202-205. Solving the equations (37) results in solving a Sylvester system. It should be noted that a calculation routine for the Matlab® software program, for solving asymptotic rejection equations, is provided with the above-mentioned work.

By comparing the equations (24) and (25) with the equation (34), it can be seen that this structure with an increased state of the observer is not another thing that the central controller as it has been defined, provided with the Youla parameter, but with the notations of the equations (24) and (25):

$$A_Q=G_2-Kf_2\cdot W_2$$

$$B_Q=Kf_2$$

$$C_Q=KC_2 \quad (38)$$

It should be noted that these equations are valid because it has been chosen Kf=0.

Figure 14:
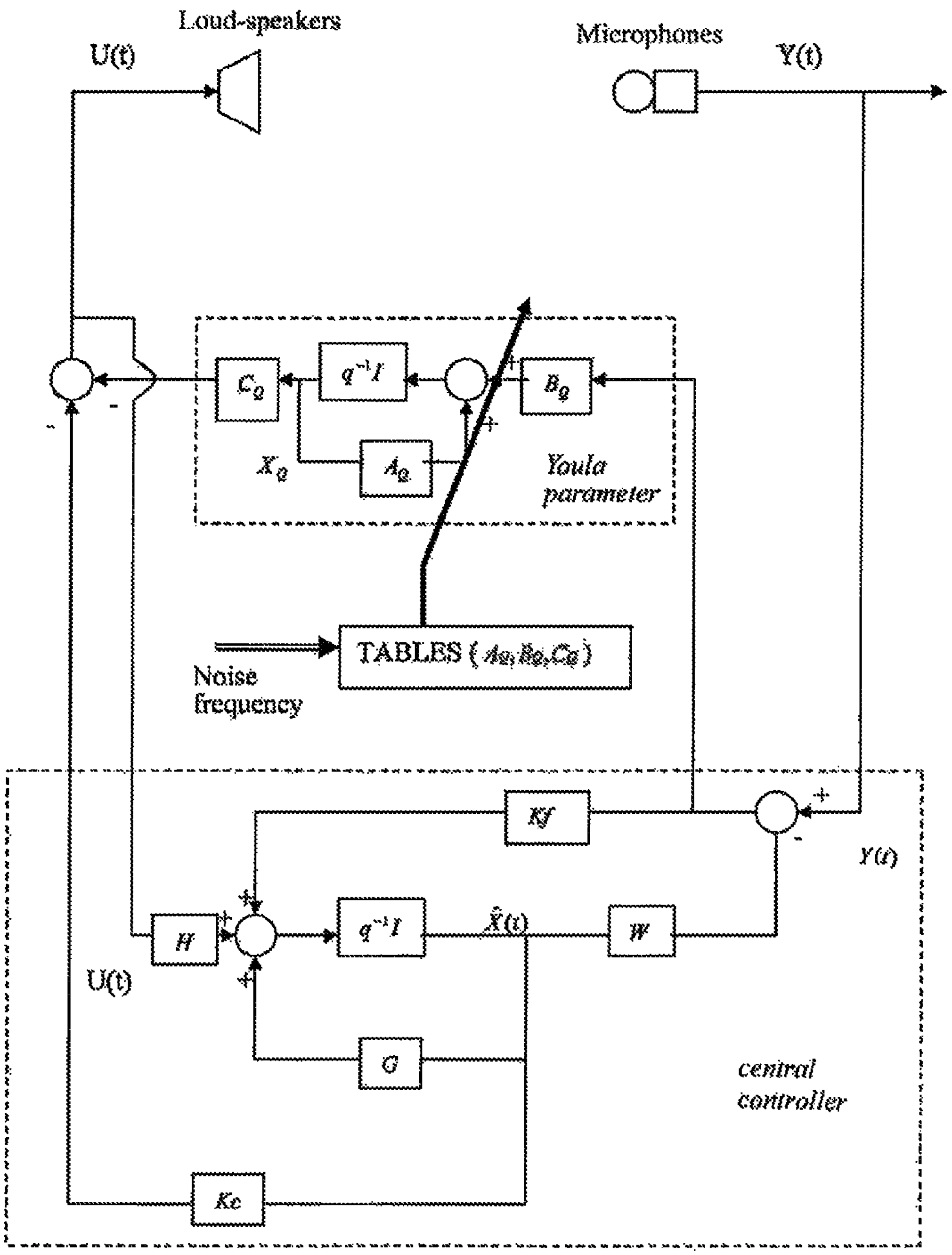
FIG. 14 is a representation as a block-diagram of the control law, central controller+Youla parameter, used in real time for noise attenuation, in the MIMO, multi-inputs-multi-outputs-variables case.

Therefore, for each disturbance frequency, the coefficients of $A_Q$, $B_Q$, $C_Q$, can be calculated during the setting of the control law and stored in tables so as to be called, in use phase, as a function of fpert, on the real time calculator. FIG. 14 shows the diagram of application of the control law in the use phase, in real time, in the programmable calculator.

The Youla block Q can be implemented as a transfer matrix so as to minimize the number of varying coefficients in this block. Such an operation can be performed, for example, by means of the routine "ss2tf" of Matlab®.

As seen above, the setting parameters of the control law lie in the choice of the control poles (by the parameters of Kc) that have an effect on the robustness of the control law. For each frequency, it is possible to choose the damping factors $\varsigma_{1i}$, $\varsigma_{2i}$ of the continuous transfer functions of the second order that have an effect on the frequency widths and depth of the disturbance rejections at the frequency fpert.

It should be noted that the robustness of the loop control can be evaluated by the calculation of the infinite norm of the transfer matrix between P(t) and Y(t) (generalization of the SISO, single input single output, mono-variable case). As the calculation of the infinite norm of a transfer matrix is performed by calculation of the singular values of said transfer matrix, it is here again possible to use the Matlab® software program and in particular the function "SIGMA" of the "control toolbox".

Those setting possibilities generalize the setting possibilities of the SISO, single input single output, mono-variable case.

To summarize, the control law (central controller+Youla parameter) intended to be applied to an electroacoustic model of a vehicle passenger compartment, in the MIMO, multi-inputs-multi-outputs-variables case, is obtained by the following steps:

- obtaining an electroacoustic model of the vehicle passenger compartment, which is linear, MIMO, multi-inputs-multi-outputs-variables, in the form of a state representation, calculated by identification,
- synthetizing a central controller as a state observer and feedback of estimated state, with Kf chosen as Kf=0,
- choosing the coefficients of Kc that correspond to high-frequency poles to ensure the robustness of the control law (possibly by LQ optimization and in particular B-type LQ optimization),
- choosing damping factors $\varsigma_{1i}$, $\varsigma_{2i}$ for a mesh of disturbance frequencies to be rejected, such mesh being performed in particular in the case in which several current frequencies of noise to be attenuated may be met over time or when the noise frequency varies over time (as for the SISO, single input single output, mono-variable case, an interpolation of the variable parameters as a function of the frequency can be performed during the use phase),
- calculating the coefficients of the Youla parameter, which are stored in tables of the calculator to be used in real time in the use phase.

It should be noted that a reduction of the number of coefficients to place in the tables can be performed by choosing all the $\varsigma_{2i}$ equal to each other for a given disturbance frequency.

Therefore, the invention implements a central controller with a Youla parameter that is in the form of an infinite impulse response filter, with at least one input and at least one output, the number of which being a function of the modes of implementation chosen (SISO, single input single output, mono-variable, MIMO, multi-inputs-multi-outputs-variables, number of sensors and transducers . . . ).

In the above-mentioned exemplary embodiments, it has been made reference to the case of rejection of a single one frequency so as to simplify the explanations. However, the invention may apply to the rejection of several frequencies in the same time, and such a case will thus be described now.

Indeed, whether it is the SISO, single input single output, mono-variable case or the MIMO, multi-inputs-multi-outputs-variables case, it is possible to reject simultaneously more than one frequency. This leads to introducing a second or even a third notch in the sensitivity function Syp. However, it results therefrom, taken into account the Bode-Freudenberg-Looze theorem, that providing one or several additional notches in the sensitivity function necessarily causes a rise of |Syp| at the other frequencies, hence a reduction of the robustness.

In the following, it will be supposed that two frequencies are rejected, but this is not in any way limitative and is given only by way of example. These two frequencies are:

- the current frequency that is designed herein fpert, to use the notations used up to now in the present document, and
- a second frequency related to fpert and that will be designed η·fpert, η being not necessarily an integer, η may be a constant without being necessarily an integer, but it may also be a function of fpert, the only condition being that the function η.(fpert) has to be continuous.

In the SISO, single input single output, mono-variable case, the Bezout equation (10) still applies:

$$S'(q^{-1})\cdot Hs(q^{-1})+q^{-d}B(q^{-1})\beta(q^{-1})=So(q^{-1})\cdot\alpha(q^{-1})$$

in which the unknowns are still $S'^{(q-1)}$ and $\beta(q^{-1})$, but this time Hs and α are such that the transfer function $Hs(q^{-1})/\alpha(q^{-1})$ results from the discretization of a continuous by the Tustin method, consisted of a product of two continuous transfer functions of the second order:

$$\frac{\dfrac{s^2}{(2\pi\cdot fpert)^2}+\dfrac{2\cdot\varsigma_{11}\cdot s}{(2\pi\cdot fpert)}+1}{\dfrac{s^2}{(2\pi\cdot fpert)^2}+\dfrac{2\cdot\varsigma_{21}\cdot s}{(2\pi\cdot fpert)}+1}\cdot\frac{\dfrac{s^2}{(2\pi\cdot\eta\cdot fpert)^2}+\dfrac{2\cdot\varsigma_{12}\cdot s}{(2\pi\cdot\eta\cdot fpert)}+1}{\dfrac{s^2}{(2\pi\cdot\eta\cdot fpert)^2}+\dfrac{2\cdot\varsigma_{22}\cdot s}{(2\pi\cdot\eta\cdot fpert)}+1}$$

Hs and α are here polynomials in $q^{-1}$ of degree 4, and $\varsigma S_{1_1}$, $\varsigma S_{1_2}$, $\varsigma S_{2_1}$, $\varsigma S_{2_2}$ are damping factors permitting, as in the case of the mono-frequency rejection, to set the width and the depth of the attenuation notch in the representative curve of the module of Syp, $\alpha(q^{-1})$ is a polynomial of order 4 and $\beta(q^{-1})$ is a polynomial of order 3. The number of variable coefficients in the control law is thus higher: there are 4 additional coefficients to be varied as a function of fpert.

In the MIMO, multi-inputs-multi-outputs-variables case, the matrix $G_{2i}$ of the equation (27) is now of dimension 4*4, i.e.:

$$G_{2i}=\begin{bmatrix}-hs_{1i} & 1 & 0 & 0\\ -hs_{2i} & 0 & 1 & 0\\ -hs_{3i} & 0 & 0 & 1\\ -hs_{4i} & 0 & 0 & 0\end{bmatrix}$$

and, also:

$$W_{2i}=[1\ 0\ 0\ 0].$$

It should be noted that the choice of the form of $G_{2i}$ $W_{2i}$ is not unique. A canonical representation of observability has been adopted here.

where $hs_{1i}$ $hs_{2i}$ $hs_{3i}$ $hs_{4i}$ are the coefficients of the numerator of a transfer function $$\frac{HS(q^{-1})}{\alpha(q^{-1})}$$

resulting from the discretization of a product of two continuous transfer functions of the second order identical to those which are used in the SISO, single input single output, mono-variable case, i.e.:

$$\frac{\dfrac{s^2}{(2\pi\cdot fpert)^2}+\dfrac{2\cdot\varsigma_{11}\cdot s}{(2\pi\cdot fpert)}+1}{\dfrac{s^2}{(2\pi\cdot fpert)^2}+\dfrac{2\cdot\varsigma_{21}\cdot s}{(2\pi\cdot fpert)}+1}\cdot\frac{\dfrac{s^2}{(2\pi\cdot\eta\cdot fpert)^2}+\dfrac{2\cdot\varsigma_{12}\cdot s}{(2\pi\cdot\eta\cdot fpert)}+1}{\dfrac{s^2}{(2\pi\cdot\eta\cdot fpert)^2}+\dfrac{2\cdot\varsigma_{22}\cdot s}{(2\pi\cdot\eta\cdot fpert)}+1}$$

with:

$$H_{si}(q^{-1})=h_{0i}+h_{1i}\cdot q^{-1}+h_{2i}(q^{-1})+h_{3i}(q^{-1})+h_{4i}(q^{-1})$$

and:

-continued $$hs_{1i} = \frac{h_{1i}}{h_{0i}}$$

$$hs_{2i} = \frac{h_{2i}}{h_{0i}}$$

$$hs_{3i} = \frac{h_{3i}}{h_{0i}}$$

$$hs_{4i} = \frac{h_{4i}}{h_{0i}}$$

It results that now:

$Kf_2$ is of dimension (4*ny,ny)

$Kc_2$ is of dimension (nu,4*ny), with $G_2$ in accordance to the equation (31), but of dimension (4ny*4ny).

The vector $\hat{X}_2$ (t) is this time of dimension (4ny*1) and the matrix $W_2$ is this time of dimension (ny*4ny). The equations of asymptotic rejection (36) and (37) remain unchanged. Solving such a MIMO, multi-inputs-multi-outputs-variables system is similar to the above-mentioned case of rejection of a single one frequency.

What has been described for a number of simultaneously rejected frequencies equal to two may possibly be extended to a higher number of frequencies. However, as explained above, the increase of the number of rejected frequencies leads to a loss of robustness rapidly becoming redhibitory.

It will be understood that the principle of the invention, central controller to which is adjoined a Youla parameter, can be applied in practice for attenuating noise differently from what have been detailed hereinabove. In particular, the type of electroacoustic model may be different, the modes of determination and/or synthesis of the central controller and of the Youla parameter may also be different and it may usefully be referred to the indicated literature for the practical implementation of these other modes.

The invention claimed is:

1. A real-time active method for attenuating, through feedback, a narrow-band noise, essentially mono-frequency at at least one determined frequency, in a vehicle passenger compartment, by emitting a sound through at least one transducer, typically a loud-speaker, controlled by a signal u(t) or U(t) according to a SISO or MIMO case respectively, generated by a programmable calculator, as a function of a signal of acoustic measurements y(t) or Y(t) according to the case, performed by at least one acoustic sensor, typically a microphone, wherein the use of a sensor corresponds to a SISO, single input single output, mono-variable, case, and the use of several sensors corresponds to a MIMO, multi-inputs-multi-outputs-variables case, and, in a first phase of design, the electroacoustic response of the unit formed by the passenger compartment, the transducer and the sensor, is modeled by an electroacoustic model as an electroacoustic transfer function that is determined and calculated, a control law being then determined and calculated from a global model of the system in which the control law is applied to the electroacoustic transfer function whose output additionally receives a noise signal to be attenuated p(t) to give the signal y(t) or Y(t) in said design phase, said control law making it possible to produce the signal u(t) or U(t) as a function of the acoustic measurements y(t) or Y(t), and in a second phase of use, said calculated control law is used in the calculator to produce the signal u(t) or U(t) then sent to the transducer as a function of the signal y(t) or Y(t) received from the sensor for attenuating said noise, characterized in that a control law is implemented, which comprises the application of a Youla parameter to a central controller and which is such that only the Youla parameter has coefficients that depend on the frequency of the noise to be attenuated in said control law, the central controller having fixed coefficients, the Youla parameter being in the form of an infinite impulse response filter, and in that, after determination and calculation of the control law, at least said variable coefficients are stored into a memory of the calculator, preferably in a table as a function the determined noise frequency(ies) p(t) used in the design phase, and in that, in the use phase, in real time:

the current frequency of the noise to be attenuated is collected, the calculator is caused to calculate the control law, comprising the central controller with the Youla parameter, using as the Youla parameter the memorized coefficients of a determined frequency corresponding to the current frequency of the noise to be attenuated.

2. A method according to claim 1, characterized in that, in the SISO, single input single output case, in the design phase:

a)—in a first time, a linear electroacoustic model is used, the electroacoustic model being in the form of a discrete rational electroacoustic transfer function, and said electroacoustic model is determined and calculated by acoustic excitation of the passenger compartment by the transducer and acoustic measurements by the sensor, then application of a linear system identification process with the measures and the model, b)—in a second time, a central controller is implemented, which is applied to the determined and calculated electroacoustic model, the central controller being in the form of a RS controller of two blocks $1/So(q^{-1})$ and, $Ro(q^{-1})$, in the central controller, the block $1/So(q^{-1})$ producing the signal u(t) and receiving as an input the inverted output signal of the block $Ro(q^{-1})$, said block $Ro(q^{-1})$ receiving as an input the signal y(t) corresponding to the sum of the noise p(t) and of the output of the electroacoustic transfer function of the electroacoustic model, and the central controller is determined and calculated, c)—in a third time, a Youla parameter is adjoined to the central controller to form the control law, the Youla parameter being in the form of a block $Q(q^{-1})$, a infinite impulse response filter, with $$Q(q^{-1}) = \frac{\beta(q^{-1})}{\alpha(q^{-1})}$$

adjoined to the central RS controller, said Youla block $Q(q^{-1})$ receiving a noise estimation obtained by calculation from the signals u(t) and y (t) and as a function of the electroacoustic transfer function and the output signal of said Youla block $Q(q^{-1})$ being subtracted from the inverted signal of $Ro(q^{-1})$ sent to the input of the block $1/So(q^{-1})$ of the central RS controller, and the Youla parameter in the control law comprising the central controller with which is associated the Youla parameter, is determined and calculated for at least one noise frequency p(t), including at least the determined frequency of the noise to be attenuated, and in that, in the use phase, in real time:

the current frequency of the noise to be attenuated is collected, the calculator is caused to calculate the control law, comprising the RS controller with the Youla parameter, using as the Youla parameter the coefficients that have been calculated for a noise frequency corresponding to the current frequency of the noise to be attenuated, the coefficients of $Ro(q^{-1})$ and $So(q^{-1})$ being fixed coefficients.

3. A method according to claim 2, characterized in that, in the design phase, the following operations are performed:

a)—in a first time, the passenger compartment is acoustically excited by applying to the transducer an excitation signal whose spectral density is substantially uniform over an effective band of frequencies, b)—in a second time, the polynomials $Ro(q^{-1})$ and $So(q^{-1})$ of the central controller are determined and calculated, so that said central controller is equivalent to a controller calculated by poles placement of the closed loop in the application of the central controller to the electroacoustic transfer function, n poles of the closed loop being placed onto the n poles of the transfer function of the electroacoustic system, c)—in a third time, the numerator and denominator of the Youla block $Q(q^{-1})$ in the control law are determined and calculated for at least one noise frequency p(t), including at least the determined frequency of the noise to be attenuated, as a function of a criterion of attenuation, the block $Q(q^{-1})$ being expressed in the form of a ratio, $\beta(q^{-1})/\alpha(q^{-1})$, so as to obtain coefficient values of the polynomials $\alpha(q^{-1})$ and $\beta(q^{-1})$ for the/each frequency, the calculation of $\beta(q^{-1})$ and $\alpha(q^{-1})$ being performed by obtaining a discrete transfer function $Hs(q^{-1})/\alpha(q^{-1})$ resulting from the discretization of a continuous transfer function of the second order, the polynomial $\beta(q^{-1})$ being calculated by solving a Bezout equation, and in that, in the use phase, in real time, the following operations are performed:

the calculator is caused to calculate the control law, fixed-coefficient central controller with variable-coefficient Youla parameter, to produce the signal u(t) sent to the transducer, as a function of the acoustic measurements y(t) and using for the Youla block $Q(q^{-1})$ the coefficient values of the polynomials $a(q^{-1})$ and $\beta(q^{-1})$ determined and calculated for a determined frequency corresponding to the current frequency.

4. A method according to claim 2, characterized in that, for the electroacoustic model is used an electroacoustic transfer function of the form:

$$\frac{y(t)}{u(t)} = \frac{q^{-d}B(q^{-1})}{A(q^{-1})}$$

where d is the number of delay sampling periods, B and A are polynomials in $q^{-1}$ of the form:

$$B(q^{-1})=b_0+b_1\cdot q^{-1}+ \dots b_{nb}\cdot q^{-nb}$$

$$A(q^{-1})=1+a_1\cdot q^{-1}+ \dots a_{na}\cdot q^{-na}$$

where $b_i$ and $a_i$ are scalar quantities, and $q^{-1}$ is the delay operator of a sampling period, and in that the calculation of the noise estimation is obtained by applying the function $q^{-d}B(q^{-1})$ to u(t) and subtracting the result from the application of y(t) to the function $\cdot A(q^{-1})$.

5. A method according to claim 2, characterized in that, for the time b), the polynomials $Ro(q^{-1})$ and $So(q^{-1})$ of the central controller are determined and calculated by a method of poles placement of the closed loop, n dominant poles of the closed loop provided with the central controller being chosen equal to the n poles of the electroacoustic transfer function and m auxiliary poles being poles located in high frequency.

6. A method according to claim 1, characterized in that, in design phase:

a)—in a first time, a linear electroacoustic model is used, wherein the electroacoustic model is in the form of a state representation of matrix blocks H, W, G and $q^{-1}\cdot I$, G being a evolution matrix, H being an input matrix, W being an output matrix, and I being the identity matrix, wherein said state representation can be expressed by a recurrence equation:

$$X(t+Te)=G\cdot X(t)+H\cdot U(t)$$

$$Y(t)=W\cdot X(t)$$

with X(t): state vector, U(t): input vector; Y(t): output vector, and said electroacoustic model is determined and calculated by acoustic excitation of the passenger compartment by the transducers and acoustic measurements by the sensors, then application of a linear system identification process with the measures and the model, b)—in a second time, a central controller applied to the determined and calculated model is implemented, the central controller being in the form of a state observer and feedback of estimated state, that iteratively expresses, $\hat{X}$, a state vector of the observer, as a function of Kf, a gain of the observer, Kc a vector of feedback on the estimated state, as well as the previously determined and calculated electroacoustic model, i.e.:

$$\hat{X}(t+Te)=G\cdot\hat{X}(t)+H\cdot U(t)+Kf\cdot(Y(t)-W\cdot\hat{X}(t))$$

with a control $U(t)=-Kc\cdot\hat{X}(t)$ and said central controller is determined and calculated, c)—in a third time, a Youla parameter is adjoined to the central controller to form the control law, the Youla parameter being in the form of a MIMO, multi-inputs-multi-outputs-variables, block Q, of state matrices AQ, BQ, CQ, adjoined to the central controller also expressed in the form of a state representation, block Q whose output added to the output of the central controller produces a signal that forms the opposite of U(t), and whose input receives the signal Y(t) from which is subtracted the signal $W\cdot\hat{X}(t)$, and the Youla parameter in the control law comprising the central controller with which is associated the Youla parameter is determined and calculated for at least one noise frequency p(t), including at least the determined frequency of the noise to be attenuated, the calculation of the coefficients of the matrices AQ, BQ, CQ being performed by obtaining discrete transfer functions $Hsi(q^{-1})/\alpha i(q^{-1})$ resulting from the discretization of continuous transfer functions of the second order and by placing poles, as well as solving equations of asymptotic rejection, and in that, in the use phase, in real time:

the current frequency of the noise to be attenuated is collected, the calculator is caused to calculate the control law, comprising the fixed-coefficient central controller with the variable-coefficient Youla parameter, using as the Youla parameter the coefficients that have been calculated for a noise frequency corresponding to the current frequency of the noise to be attenuated.

7. A method according to claim 6, characterized in that, in the design phase, the following operations are performed:

a)—in a first time, the passenger compartment is acoustically excited by applying to the transducers excitation signals whose spectral density is substantially uniform over an effective band of frequencies, the excitation signals being de-correlated from each other, b)—in a second time, the central controller is determined and calculated so that it is equivalent to a controller with a state observer and a feedback on the calculated state by poles placement in the application of the central controller to the electroacoustic transfer function, wherein, for that purpose, a null observer gain is chosen, i.e. Kf=0, and a gain of state feedback Kc is chosen so as to ensure the robustness of the control law provided with the Youla parameter, by means of a LQ optimization, c)—in a third time, considering a representation of increased state observer, the coefficients of the Youla block Q in the control law are determined and calculated for at least one noise frequency P(t) including at least the determined frequency of the noise to be attenuated, as a function of criterion of attenuation, so as to obtain coefficient values of the Youla parameter for the/each frequency, and in that, in the use phase, in real time, the following operations are performed:

the calculator is caused to calculate the control law, fixed-coefficient central controller with variable-coefficient Youla parameter, to produce the signal U(t) sent to the transducers, as a function of the acoustic measurements Y(t) and using for the Youla parameter the coefficient values determined and calculated for a determined frequency corresponding to the current frequency.

8. A method according to claim 2, characterized in that the method is adapted to a set of determined frequencies of noise to be attenuated, and the time c) is repeated for each of the determined frequencies, and in that, in the use phase, when no one of the determined frequencies corresponds to the current frequency of the noise to be attenuated, an interpolation is made at said current frequency for the coefficient values of the Youla block Q, based on the coefficient values of said Youla block Q that are known for the determined frequencies.

9. A method according to claim 2, characterized in that the signals are sampled at a frequency Fe and, at the time a), the effective band of frequencies used for the excitation signal is substantially equal to [0, Fe/2].

10. A method according to claim 2, characterized in that, before the use phase, a fourth time d) is added to the design phase, for verifying the stability and the robustness of the electroacoustic system model and of the control law, central controller with Youla parameter, previously obtained at the times a) to c), by making a simulation of the control law obtained at times b) and c), applied to the electroacoustic model obtained at the time a), for the determined frequency(ies), and when a predetermined criterion of stability and/or robustness is not respected, at least the time c) is reiterated by modifying the criterion of attenuation.

11. A method according to claim 1, characterized in that the design phase is a preliminary phase and it is performed once, preliminary to the use phase, with memorization of the determination and calculation results for use in the use phase.

12. A method according to claim 1, characterized in that the current frequency of the noise to be attenuated is collected from a measurement of a motor revolution counter of the vehicle.

13. A method according to claim 1, characterized in that the noise is at one determined frequency fpert.

14. A method according to claim 1, characterized in that the noise is at two determined frequencies, with a first frequency fpert, and a second frequency $\eta \cdot$fpert, $\eta$ being either constant or varying continuously with fpert.

15. A device specially adapted for the implementation of the method according to claim 1, to attenuate a narrow-band noise, essentially mono-frequency at at least one determined frequency, wherein the device comprises at least one transducer, typically a loud-speaker, controlled with a signal generated by a programmable calculator, as a function of a signal of acoustic measurements performed by at least one acoustic sensor, typically a microphone, wherein a control law has been determined and calculated in a first phase of design, said calculated control law being used, in a second phase of use, in the calculator, to produce a signal sent to the transducer, as a function of the signal received from the sensor for attenuation of said noise, and characterized in that it comprises means for implementing, in the calculator, a control law comprising the application of Youla parameter to a central controller, wherein only one variable-coefficient transfer block corresponds to the Youla parameter having coefficients that depend on the frequency of the noise to be attenuated in said control law, the central controller having fixed coefficients, and a memory of the calculator stores at least said variable coefficients, preferably in a table as a function of the determined noise frequency(ies) p(t) used in the design phase.

16. A method according to claim 3, characterized in that, for the electroacoustic model is used an electroacoustic transfer function of the form:

$$\frac{y(t)}{u(t)} = \frac{q^{-d}B(q^{-1})}{A(q^{-1})}$$

where d is the number of delay sampling periods, B and A are polynomials in $q^{-1}$ of the form:

$$B(q^{-1})=b_0+b_1 \cdot q^{-1}+ \ldots b_{nb} \cdot q^{-nb}$$

$$A(q^{-1})=1+a_1 \cdot q^{-1}+ \ldots a_{na} \cdot q^{-na}$$

where $b_i$ and $a_i$ are scalar quantities, and $q^{-1}$ is the delay operator of a sampling period, and in that the calculation of the noise estimation is obtained by applying the function $q^{-d}B(q^{-1})$ to u(t) and subtracting the result from the application of y(t) to the function $\cdot A(q^{-1})$.

17. A method according to claim 3, characterized in that, for the time b), the polynomials $Ro(q^{-1})$ and $So(q^{-1})$ of the central controller are determined and calculated by a method of poles placement of the closed loop, n dominant poles of the closed loop provided with the central controller being chosen equal to the n poles of the electroacoustic transfer function and m auxiliary poles being poles located in high frequency.

18. A method according to claim 4, characterized in that, for the time b), the polynomials $Ro(q^{-1})$ and $So(q^{-1})$ of the central controller are determined and calculated by a method of poles placement of the closed loop, n dominant poles of the closed loop provided with the central controller being chosen equal to the n poles of the electroacoustic transfer function and m auxiliary poles being poles located in high frequency.

* * * * *